United States Patent
Bajo

(10) Patent No.: US 12,350,829 B2
(45) Date of Patent: Jul. 8, 2025

(54) SYSTEMS AND METHODS FOR CONSTRAINED MOTION CONTROL OF MEDICAL INSTRUMENTS

(71) Applicant: Auris Health, Inc., Redwood City, CA (US)

(72) Inventor: Andrea Bajo, Palo Alto, CA (US)

(73) Assignee: Auris Health, Inc., Redwood City, CA (US)

( * ) Notice: Subject to any disclaimer, the term of this patent is extended or adjusted under 35 U.S.C. 154(b) by 1062 days.

(21) Appl. No.: 17/154,352

(22) Filed: Jan. 21, 2021

(65) Prior Publication Data

US 2021/0299862 A1  Sep. 30, 2021

Related U.S. Application Data

(60) Provisional application No. 63/000,093, filed on Mar. 26, 2020.

(51) Int. Cl.
| | |
|---|---|
| *B25J 9/16* | (2006.01) |
| *A61B 34/00* | (2016.01) |
| *A61B 34/30* | (2016.01) |

(52) U.S. Cl.
CPC .............. *B25J 9/1607* (2013.01); *A61B 34/30* (2016.02); *A61B 34/76* (2016.02); *B25J 9/1633* (2013.01); *B25J 9/1664* (2013.01)

(58) Field of Classification Search
CPC ..... B25J 9/00; B25J 9/16; B25J 9/1602; B25J 9/1628; B25J 9/1607; B25J 9/1633;
(Continued)

(56) References Cited

U.S. PATENT DOCUMENTS

| 4,980,625 A | 12/1990 | Shimada |
| 8,120,301 B2 | 2/2012 | Goldberg et al. |

(Continued)

FOREIGN PATENT DOCUMENTS

| KR | 1020140136828 A | 12/2014 | |
| WO | WO2000060521 A1 * | 10/2000 | ............. A61B 34/30 |

OTHER PUBLICATIONS

International Search Report and Written Opinion for Application No. PCT/IB2021/050468, dated May 6, 2021, 9 pages.

(Continued)

*Primary Examiner* — Khoi H Tran
*Assistant Examiner* — Sarah A Tran
(74) *Attorney, Agent, or Firm* — Frost Brown Todd LLP

(57) ABSTRACT

Systems and methods for constrained motion control of medical instruments are provided. In one aspect, a robotic system includes an instrument having an end effector, a robotic arm configured to control movement of the instrument and the end effector, and an input device configured to receive an input for controlling movement of the instrument and end effector. The instrument is capable of moving in a different number of degrees-of-freedom (DOFs) than the input device. The system is configured to determine a Jacobian matrix relating the input to the input device to robotic arm commands for achieving a motion of the end effector indicated by the input, modify the Jacobian matrix via discarding at least one row of the Jacobian matrix, and determine a robotic arm command for achieving the motion of the instrument indicated by the input based on the modified Jacobian matrix.

18 Claims, 25 Drawing Sheets

(58) Field of Classification Search
CPC ...... B25J 9/1656; B25J 9/1679; B25J 9/1664; B25J 9/1643; B25J 9/1689; A61B 34/00; A61B 34/30; A61B 34/37; A61B 34/70; A61B 34/76; A61B 2017/00477; A61B 2034/301; A61B 17/00; G05B 2219/00; G05B 2219/30; G05B 2219/40; G05B 2219/40182
USPC .......................................................... 700/263
See application file for complete search history.

(56) References Cited

U.S. PATENT DOCUMENTS

| | | | |
|---|---|---|---|
| 8,130,907 | B2 | 3/2012 | Maurer, Jr. et al. |
| 8,170,716 | B2 | 5/2012 | Coste-Maniere et al. |
| 8,620,473 | B2 | 12/2013 | Diolaiti et al. |
| 9,333,042 | B2 | 5/2016 | Diolaiti et al. |
| 2011/0040306 | A1 | 2/2011 | Prisco |
| 2012/0245736 | A1* | 9/2012 | Bosscher ............... B25J 9/1607 700/262 |
| 2015/0223897 | A1 | 8/2015 | Kostrzewski et al. |
| 2016/0100900 | A1 | 4/2016 | Madhani et al. |
| 2016/0213435 | A1* | 7/2016 | Hourtash ............... A61B 34/37 |
| 2019/0105117 | A1* | 4/2019 | Brisson ................. A61B 34/30 |

OTHER PUBLICATIONS

Corke, P. (2017). Manipulator Velocity. In: Robotics, Vision and Control. Springer Tracts in Advanced Robotics, vol. 118. Springer, Cham. https://doi.org/10.1007/978-3-319-54413-7_8.
European Extended Search Report and Written Opinion dated Jun. 13, 2024, for Application No. 21777100.5, 14 pages.

* cited by examiner

SYSTEMS AND METHODS FOR CONSTRAINED MOTION CONTROL OF MEDICAL INSTRUMENTS

CROSS-REFERENCE TO RELATED APPLICATION(S)

This application claims the benefit of U.S. Provisional Application No. 63/000,093, filed Mar. 26, 2020, which is hereby incorporated by reference in its entirety.

TECHNOLOGICAL FIELD

The systems and methods disclosed herein are directed to systems and methods for controlling medical instruments, and more particularly to constrained motion control of medical instruments.

BACKGROUND

Medical procedures, such as laparoscopy, may involve accessing an internal region of a patient using one or more robotic arms to insert medical instrument(s) into the internal region of the patient. In a laparoscopic procedure, the medical instrument(s) can be inserted into the internal region through a laparoscopic cannula. In certain procedures, a robotically-enabled medical system may be used to control the insertion and/or manipulation of one or more medical instrument(s). The robotically-enabled medical system can have a user input configured to be manipulated by a user in a number of degrees-of-freedom (DOFs). Depending on the particular medical instrument under control of the input, the number of DOFs in which the instrument is capable of moving may be different from the number of DOFs in which the input is capable of controlling, commanding, and/or moving.

SUMMARY

The systems, methods and devices of this disclosure each have several innovative aspects, no single one of which is solely responsible for the desirable attributes disclosed herein.

In one aspect, there is provided a robotic system, comprising: an instrument having an end effector; a robotic arm configured to control movement of the instrument and the end effector; an input device configured to receive an input for controlling movement of the instrument and end effector, wherein the instrument is capable of moving in a different number of degrees-of-freedom (DOFs) than the input device; at least one processor; and at least one computer-readable memory in communication with the set of one or more processors and having stored thereon computer-executable instructions to cause the at least one processor to: determine a Jacobian matrix relating the input to the input device to robotic arm commands for achieving a motion of the end effector indicated by the input, modify the Jacobian matrix via discarding at least one row of the Jacobian matrix, and determine a robotic arm command for achieving the motion of the instrument indicated by the input based on the modified Jacobian matrix.

In another aspect, there is provided a method for controlling movement of an end effector of a medical instrument, the method comprising: receiving, via an input device, an input for controlling movement of the instrument, the instrument having a different number of DOFs than the input device; determining a Jacobian matrix relating the input to the input device to robotic arm commands for achieving a motion of the end effector indicated by the input; modifying the Jacobian matrix via discarding at least one row of the Jacobian matrix; and determining a robotic arm command for achieving the motion of the instrument indicated by the input based on the modified Jacobian matrix.

In yet another aspect, there is provided a robotic system, comprising: an instrument having an end effector; a robotic arm configured to control movement of the instrument and the end effector; an input device configured to receive an input command for controlling movement of the end effector, wherein the instrument is capable of moving in a fewer number of DOFs than the input device; at least one processor; and at least one computer-readable memory in communication with the set of one or more processors and having stored thereon computer-executable instructions to cause the at least one processor to: receive the input command for controlling movement of the end effector from the input device, modify the input command via discarding a portion of the input command corresponding to a movement of the end effector that is not achievable, and determine a robotic arm movement for controlling movement of the end effector based on the modified input command.

In still yet another aspect, there is provided a method for controlling movement of an end effector of a medical instrument, the method comprising: receiving, via an input device, an input command for controlling movement of the end effector, the end effector having a fewer number of DOFs than the input device; transforming the input command into an end effector coordinate frame; determining an end effector Jacobian matrix in the end effector coordinate frame; modifying the end effector Jacobian matrix via discarding at least one row of the end effector Jacobian matrix; and determining a robotic arm command for achieving the motion of the end effector indicated by the input based on the modified Jacobian matrix.

In yet another aspect, there is provided a robotic system, comprising: an instrument having an end effector; a robotic arm configured to control movement of the instrument and the end effector; an input device configured to receive an input for controlling movement of the instrument and end effector, wherein the instrument is capable of moving in a different number of DOFs than the input device; at least one processor; and at least one computer-readable memory in communication with the set of one or more processors and having stored thereon computer-executable instructions to cause the at least one processor to: determine a Jacobian matrix relating the input to the input device to robotic arm commands for achieving a motion of the end effector indicated by the input, the Jacobian matrix relating a frame of reference of the end effector to a world frame of reference of the robotic system, modify the Jacobian matrix via discarding at least one row of the Jacobian matrix, and determine a robotic arm command for achieving the motion of the instrument indicated by the input based on the modified Jacobian matrix.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
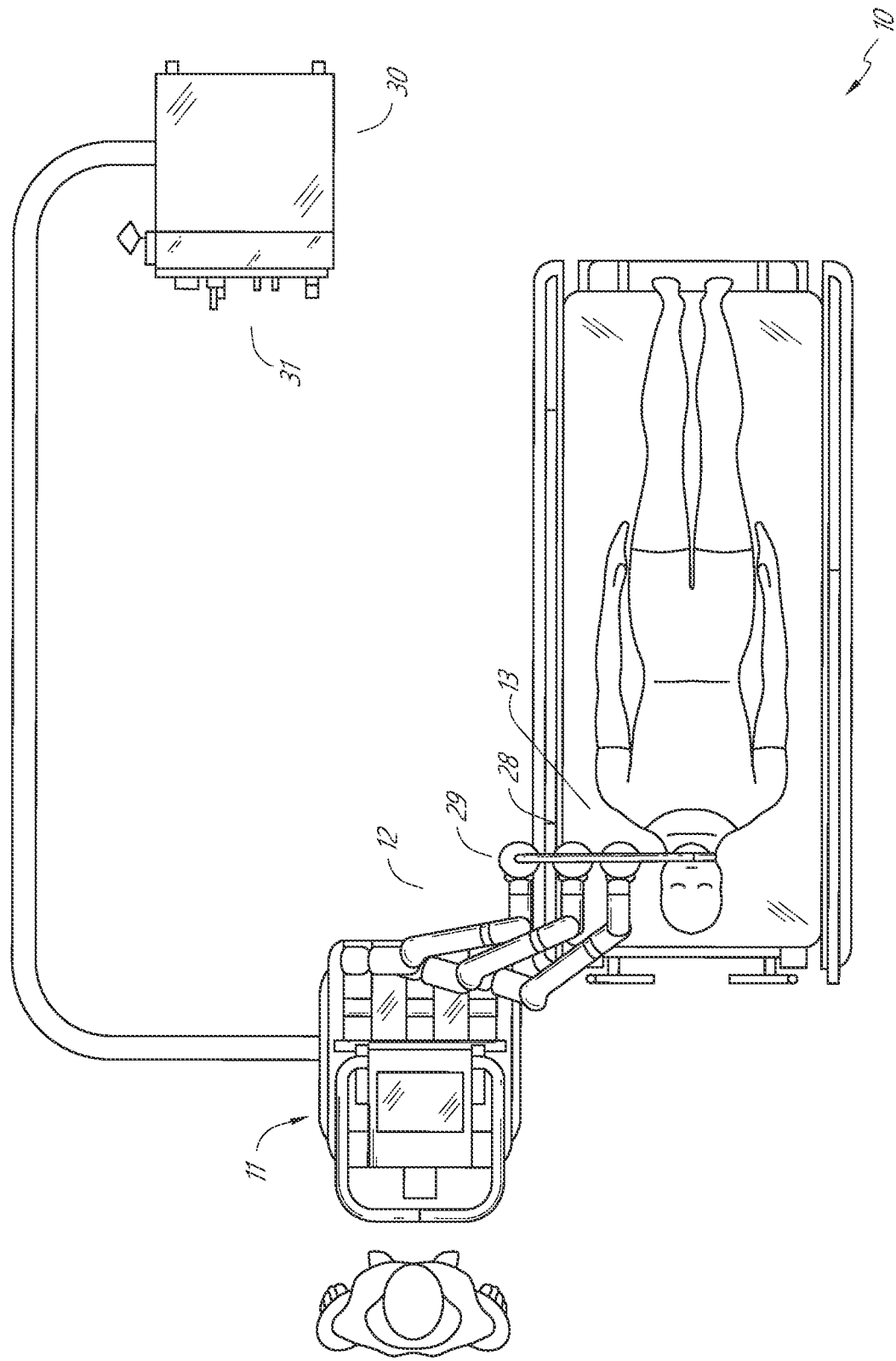
FIG. 1 illustrates an embodiment of a cart-based robotic system arranged for diagnostic and/or therapeutic bronchoscopy.
Figure 2:
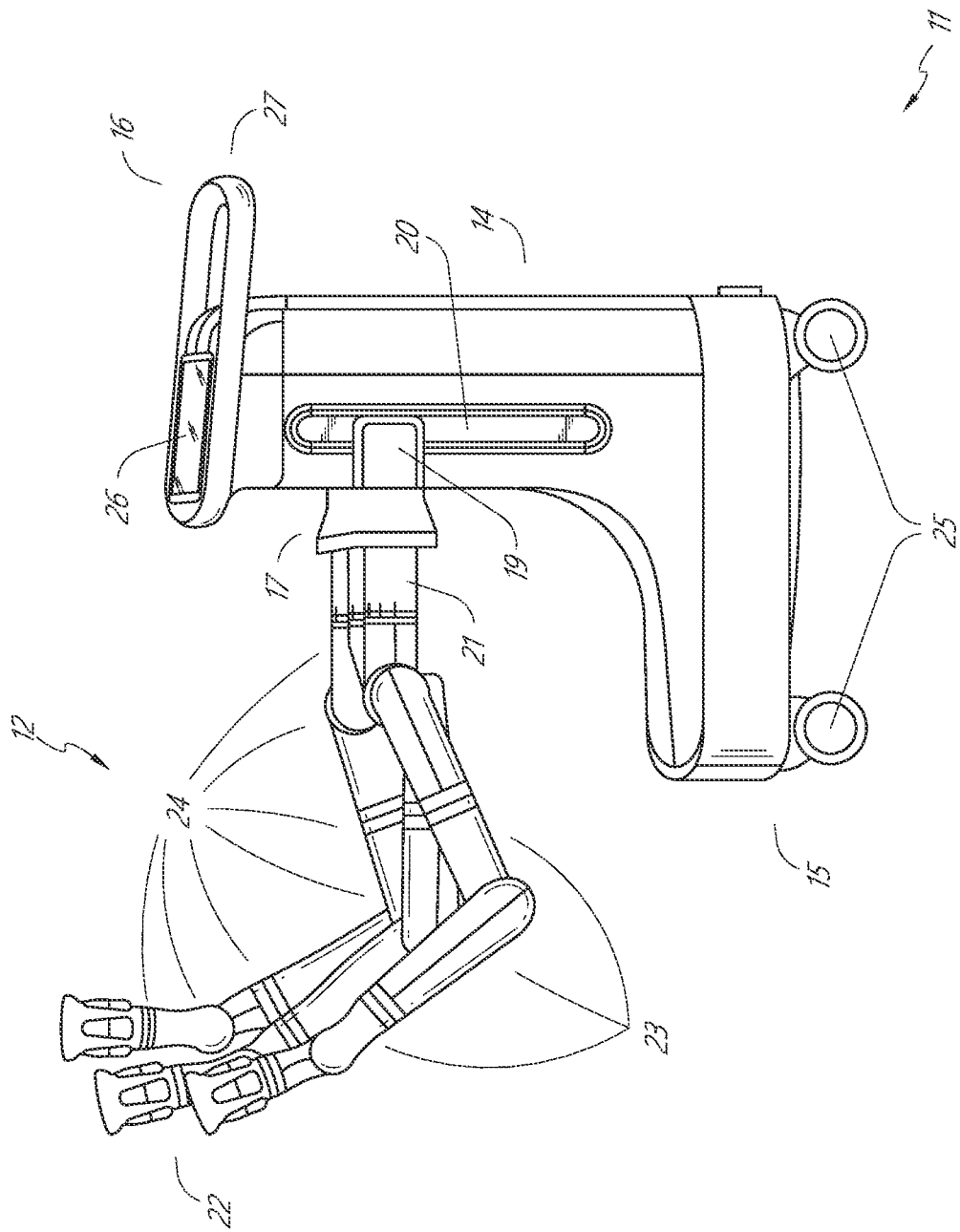
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
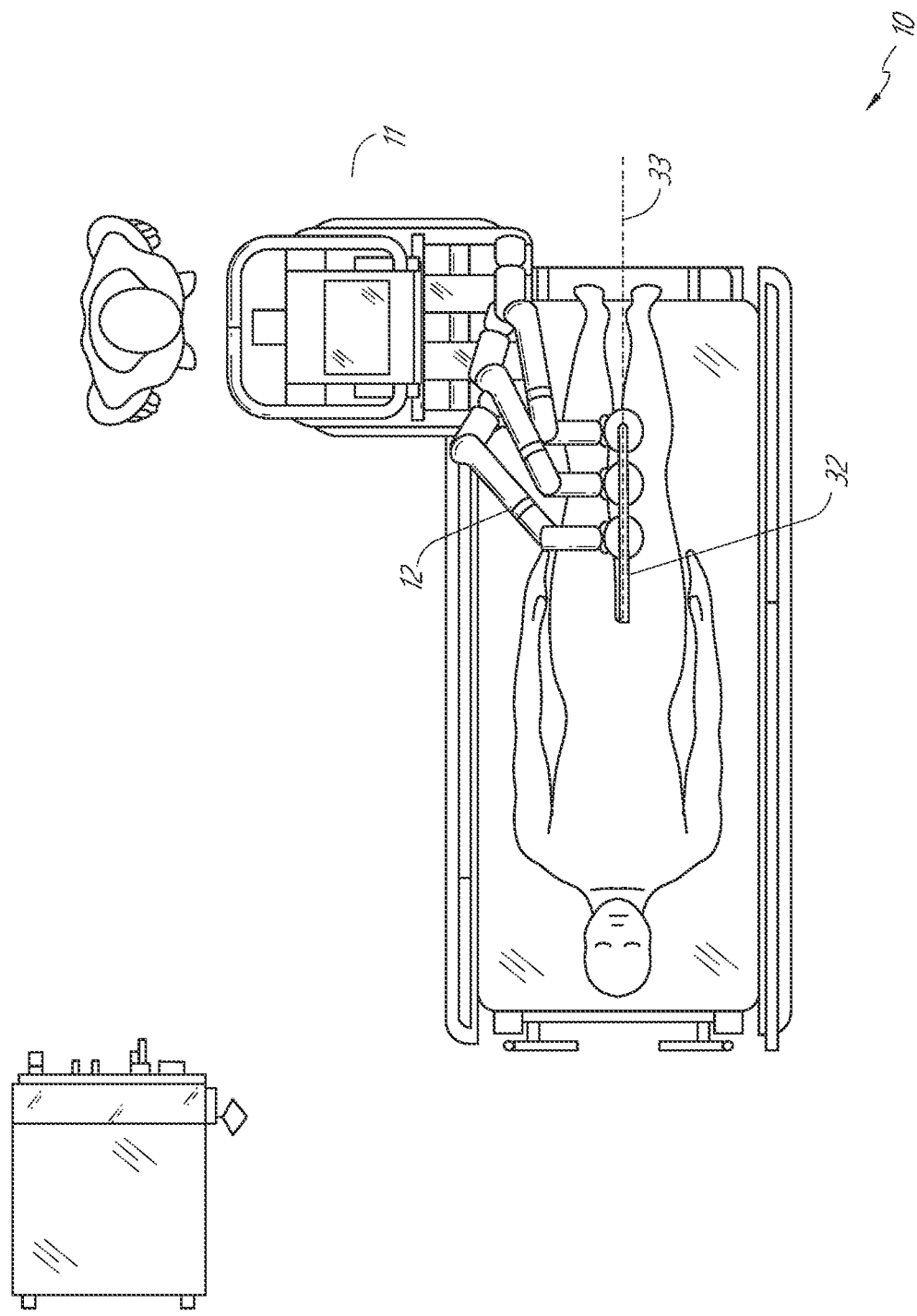
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
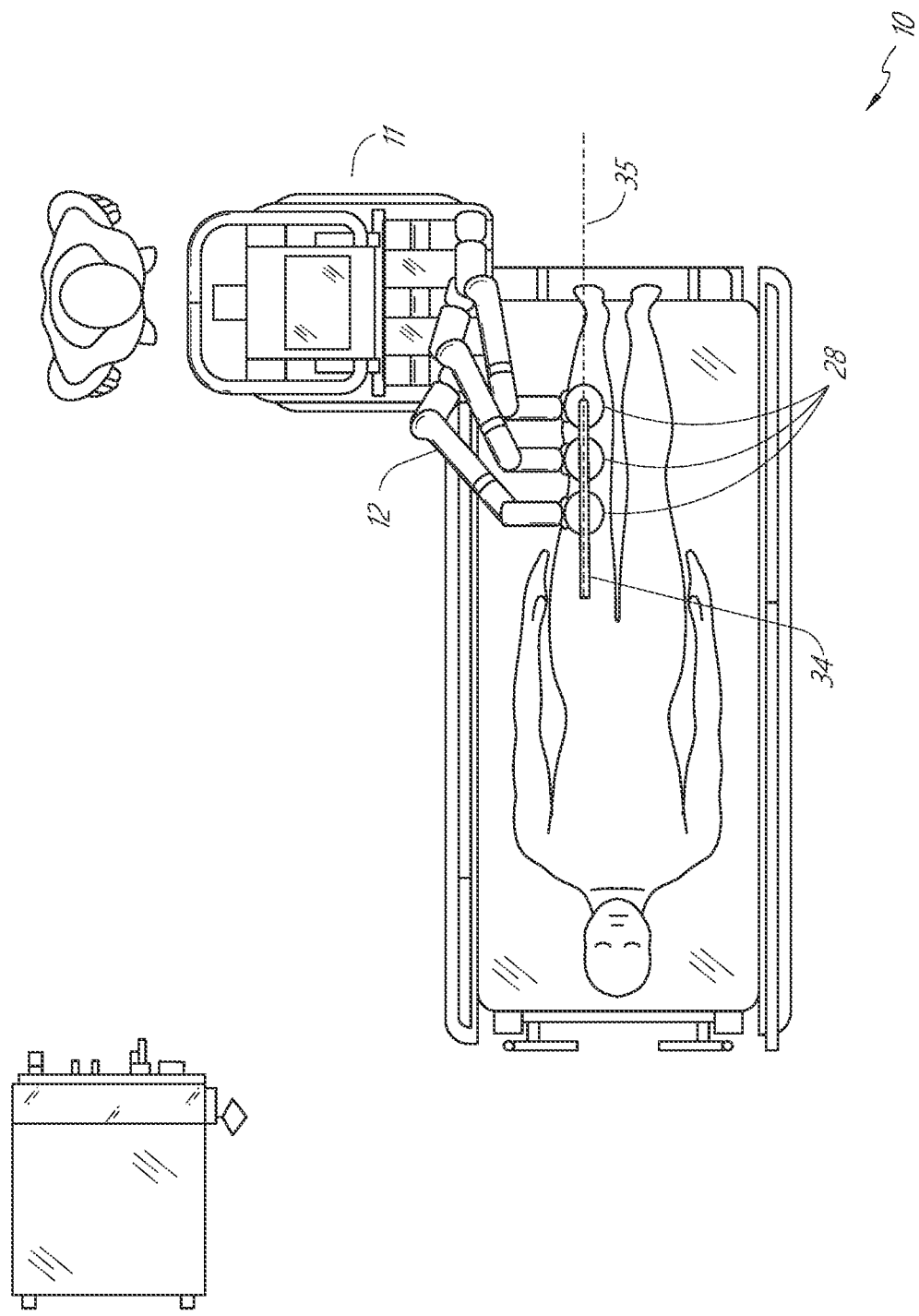
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
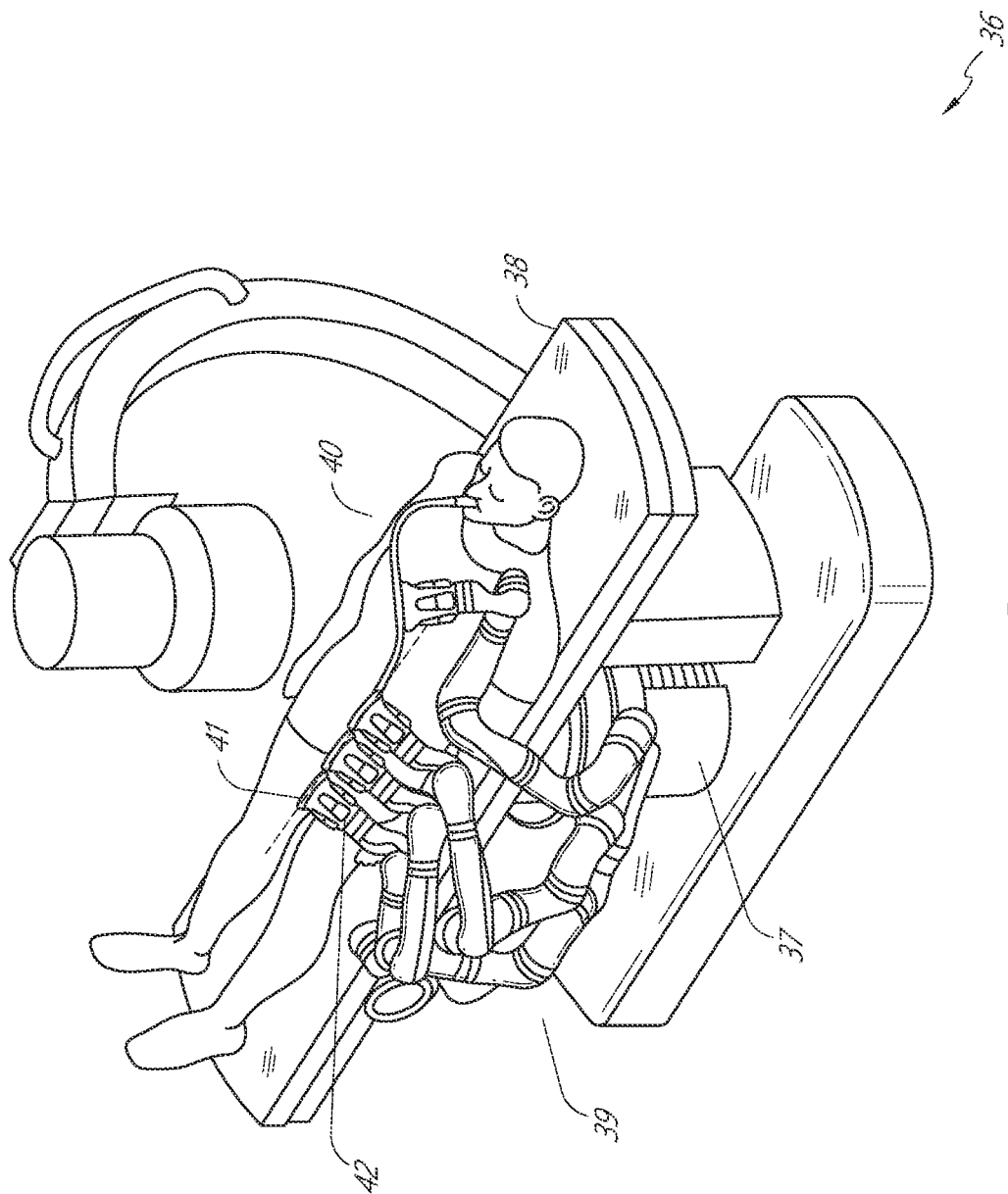
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
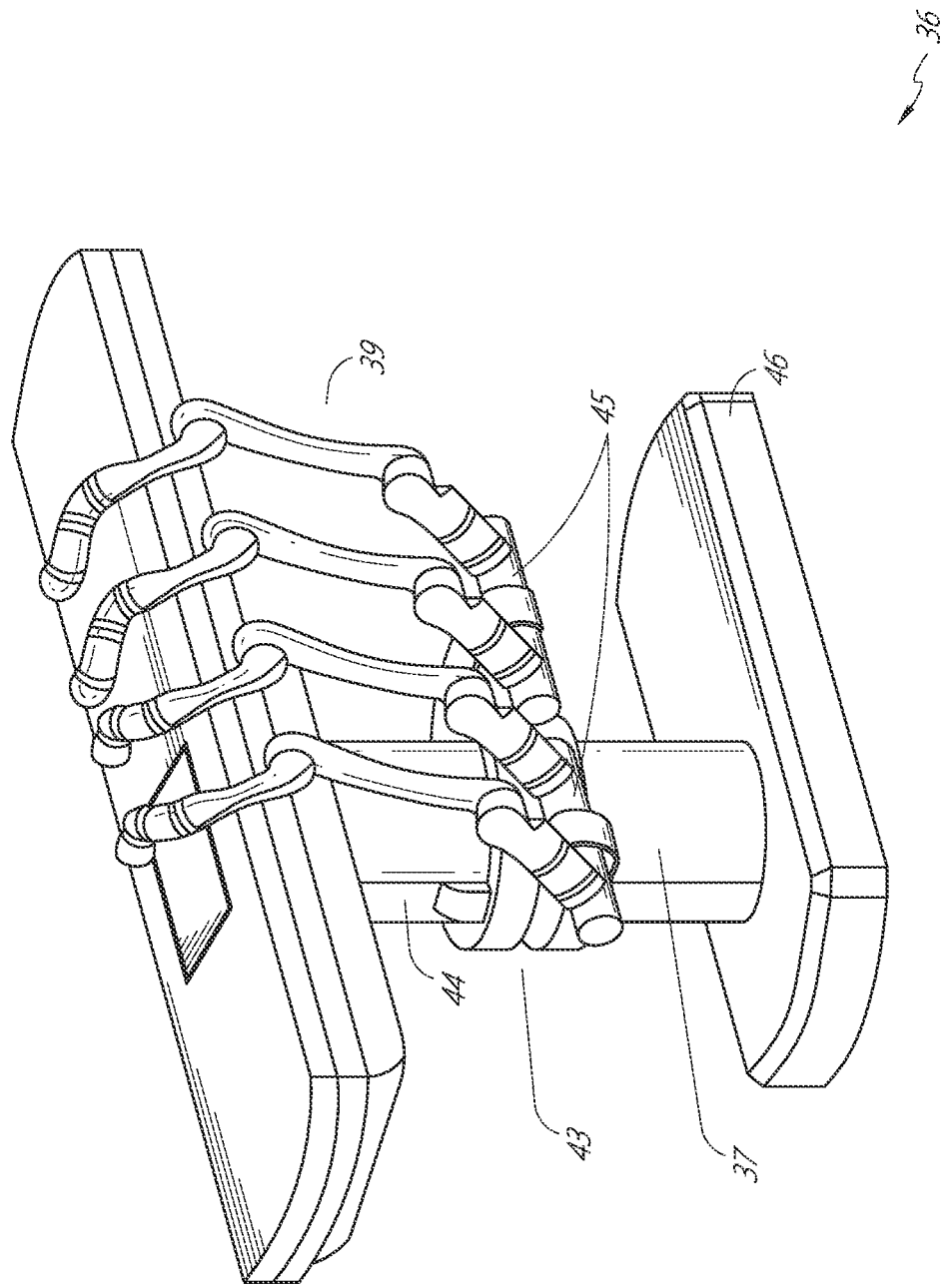
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
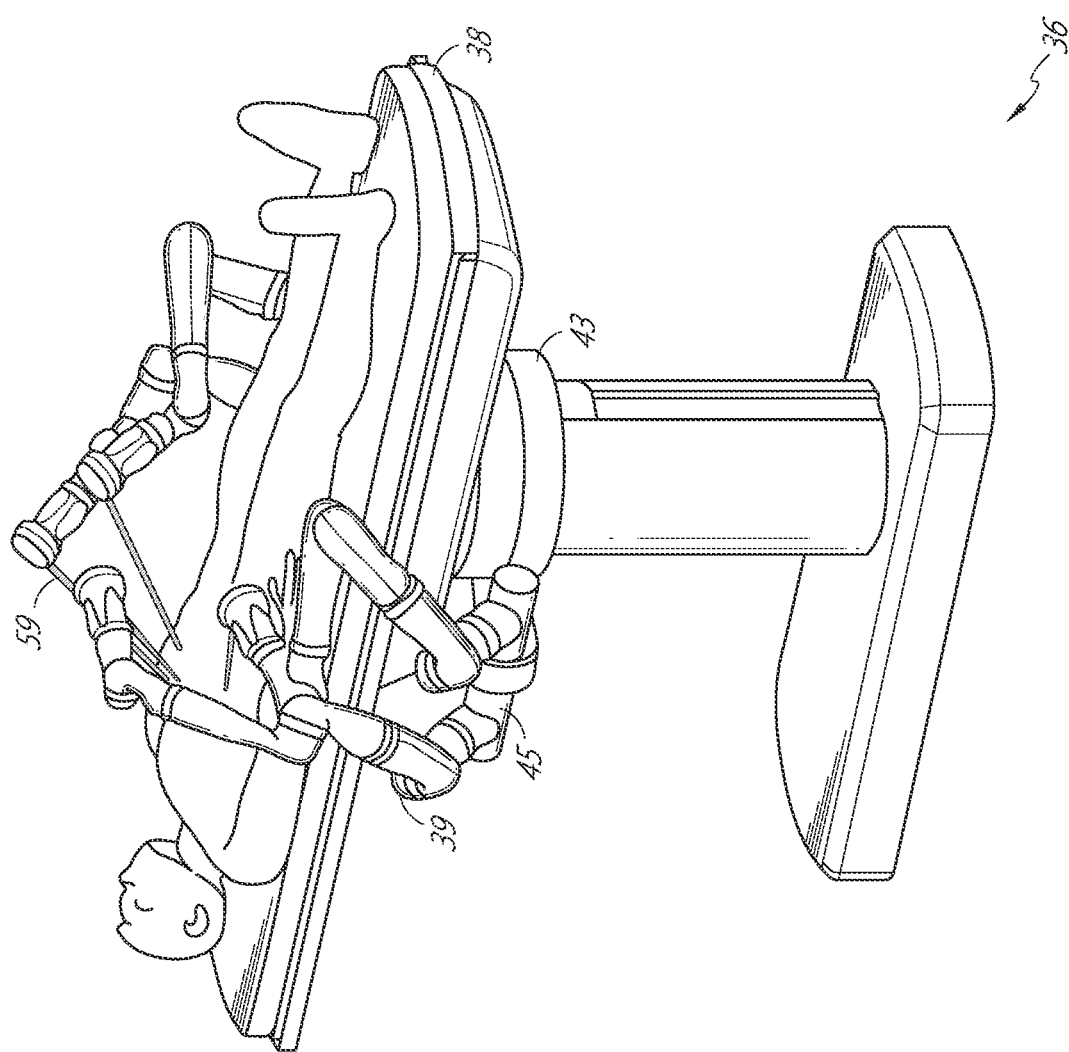
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
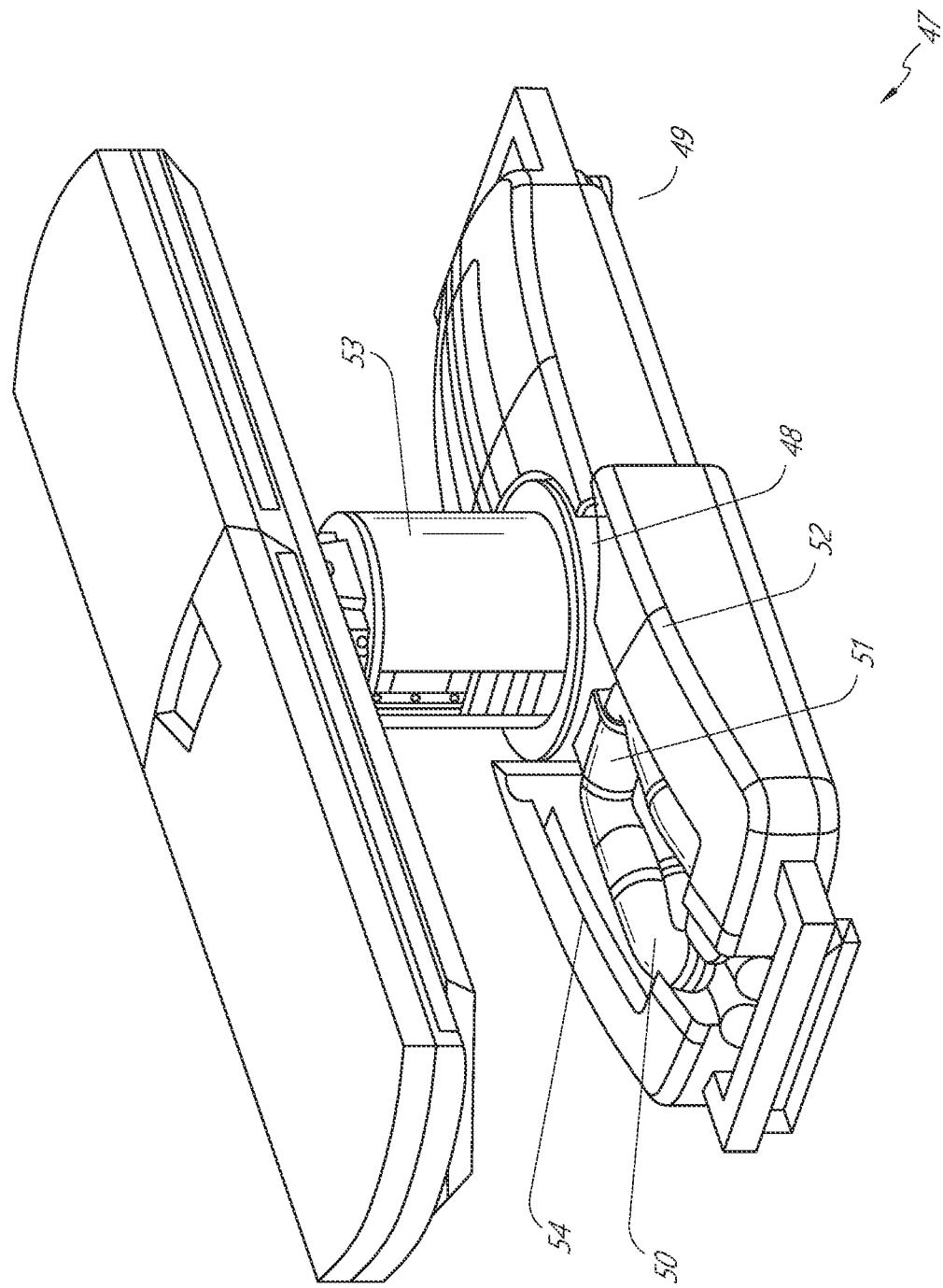
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
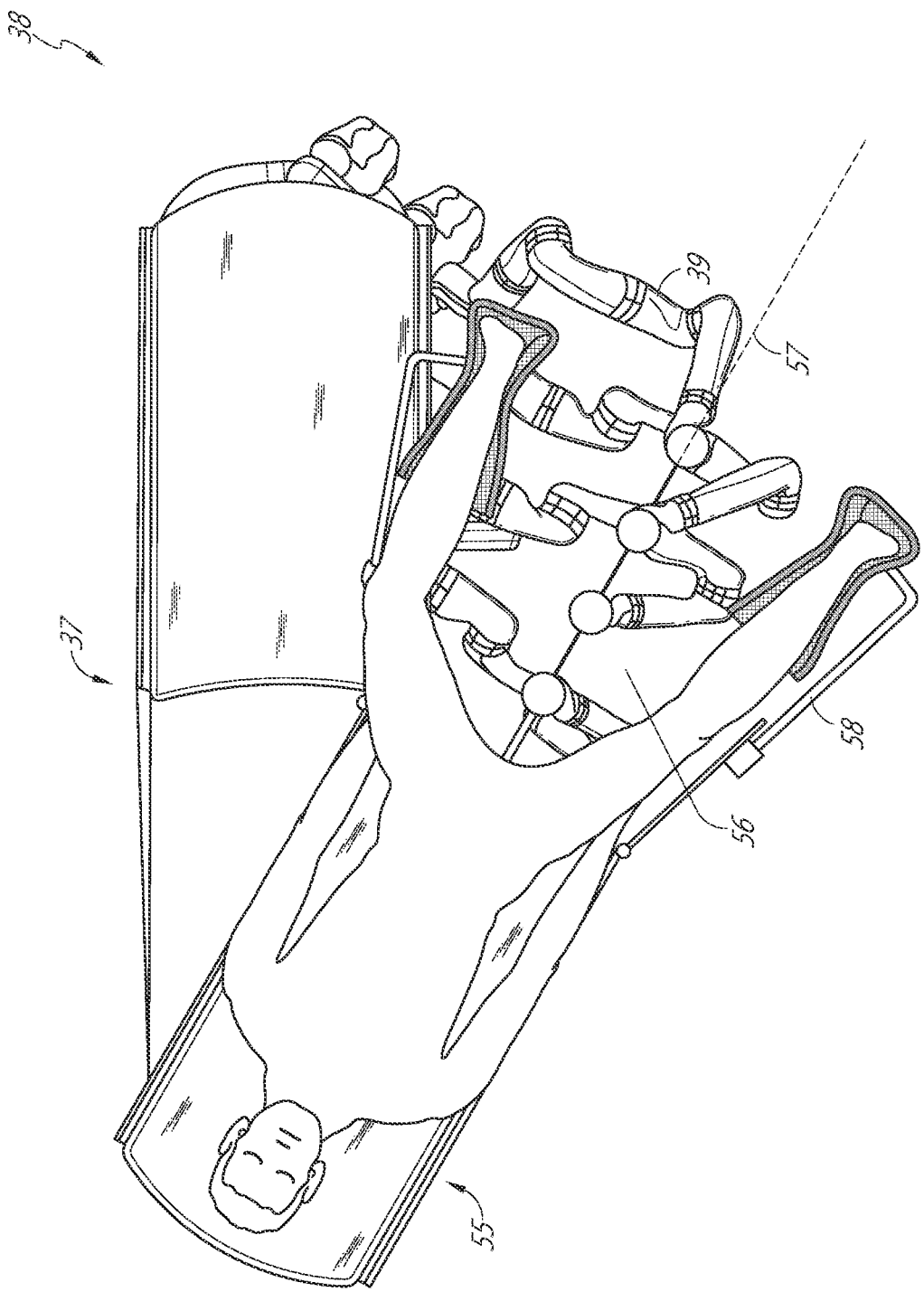
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope.

FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
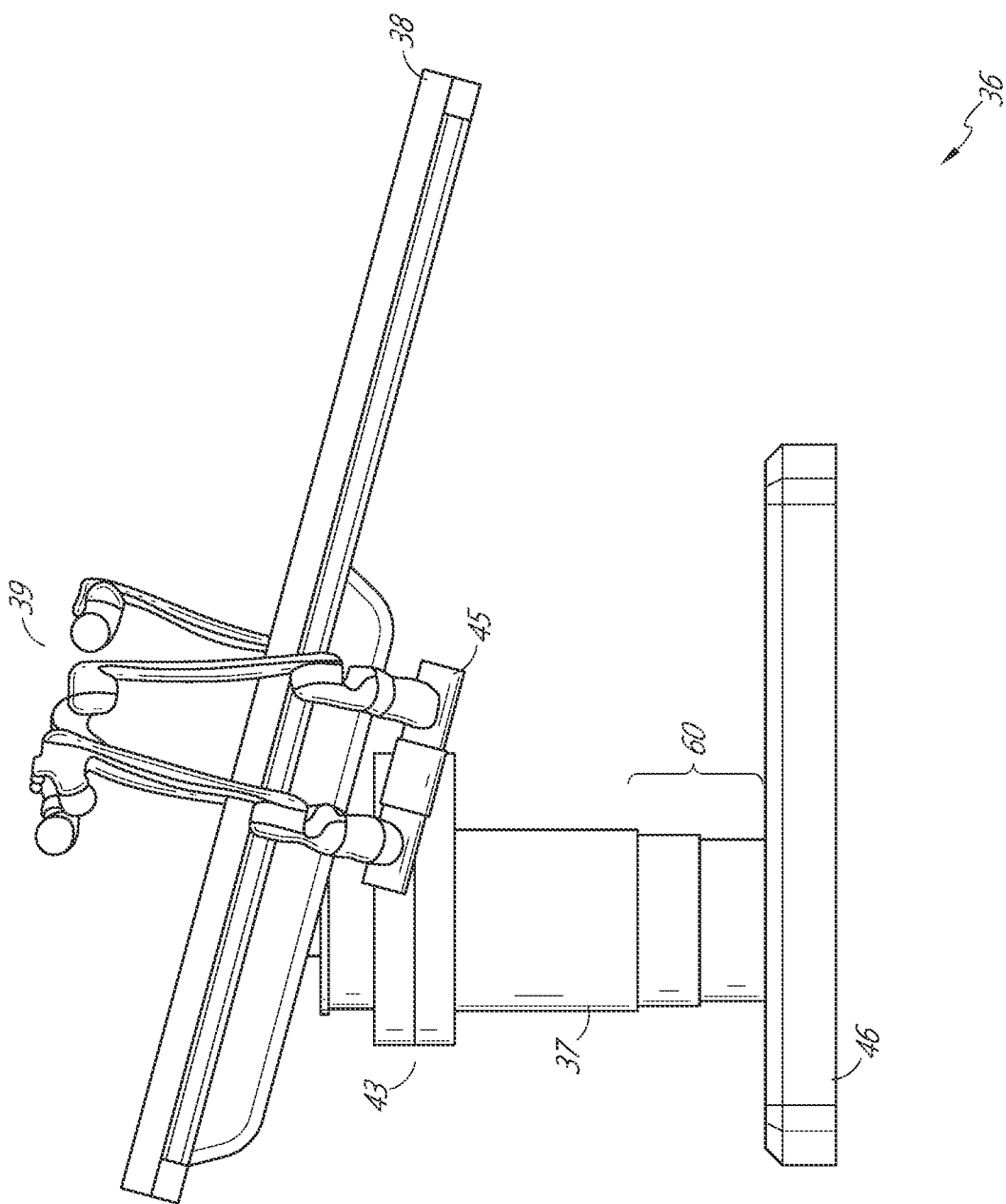
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
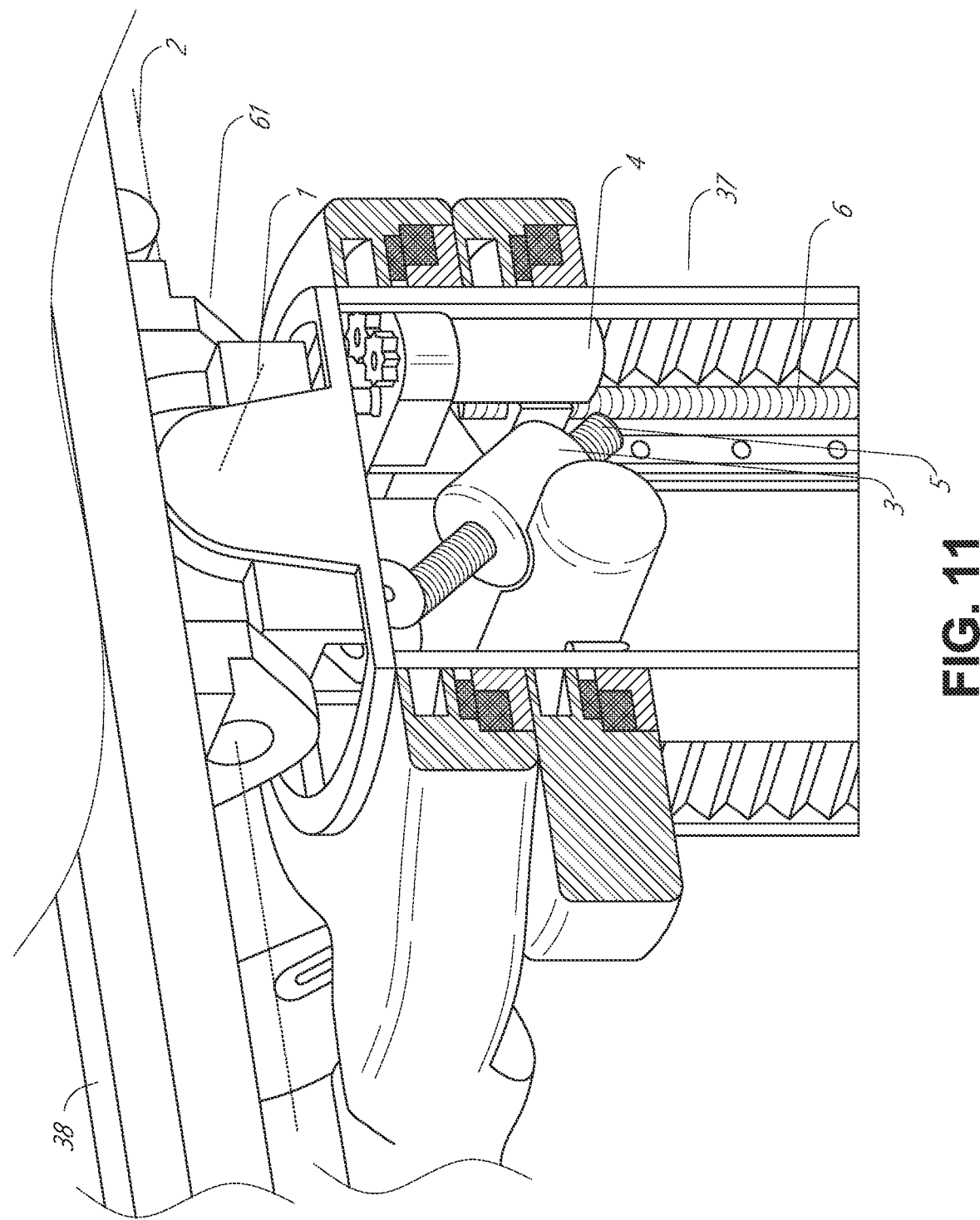
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
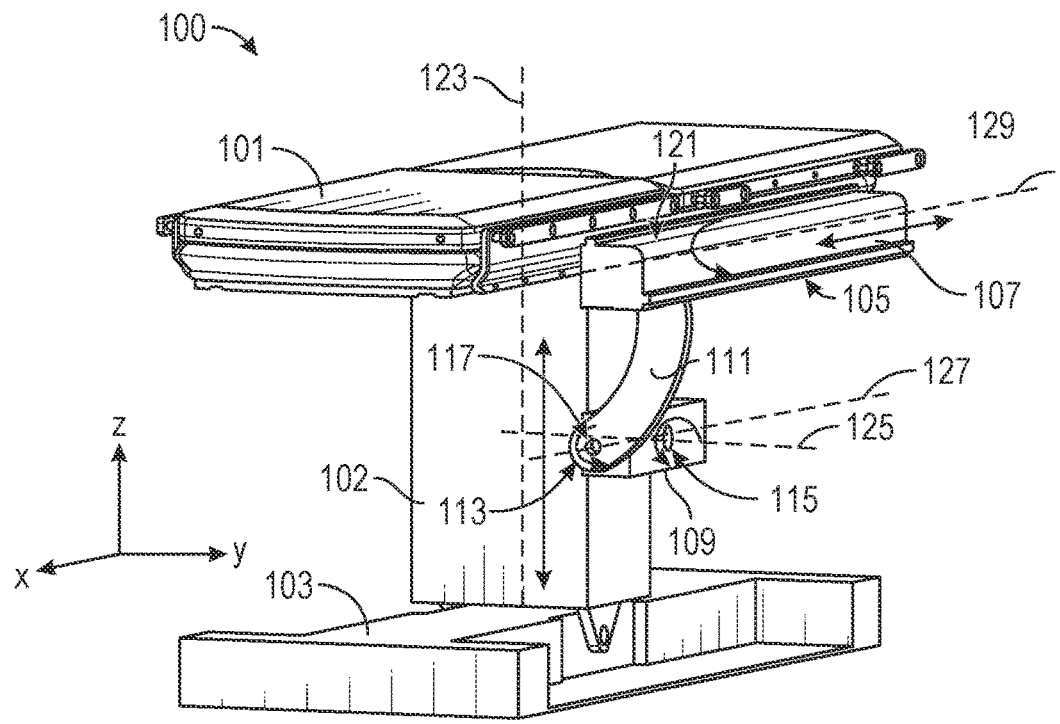
FIG. 12 illustrates an alternative embodiment of a table-based robotic system.
Figure 13:
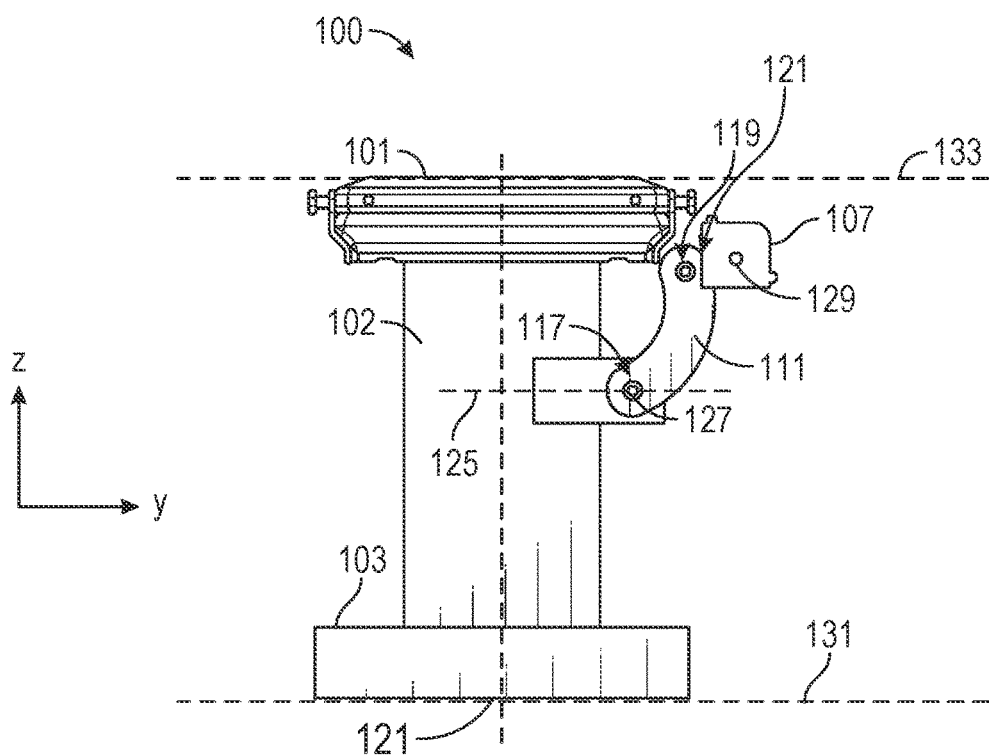
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
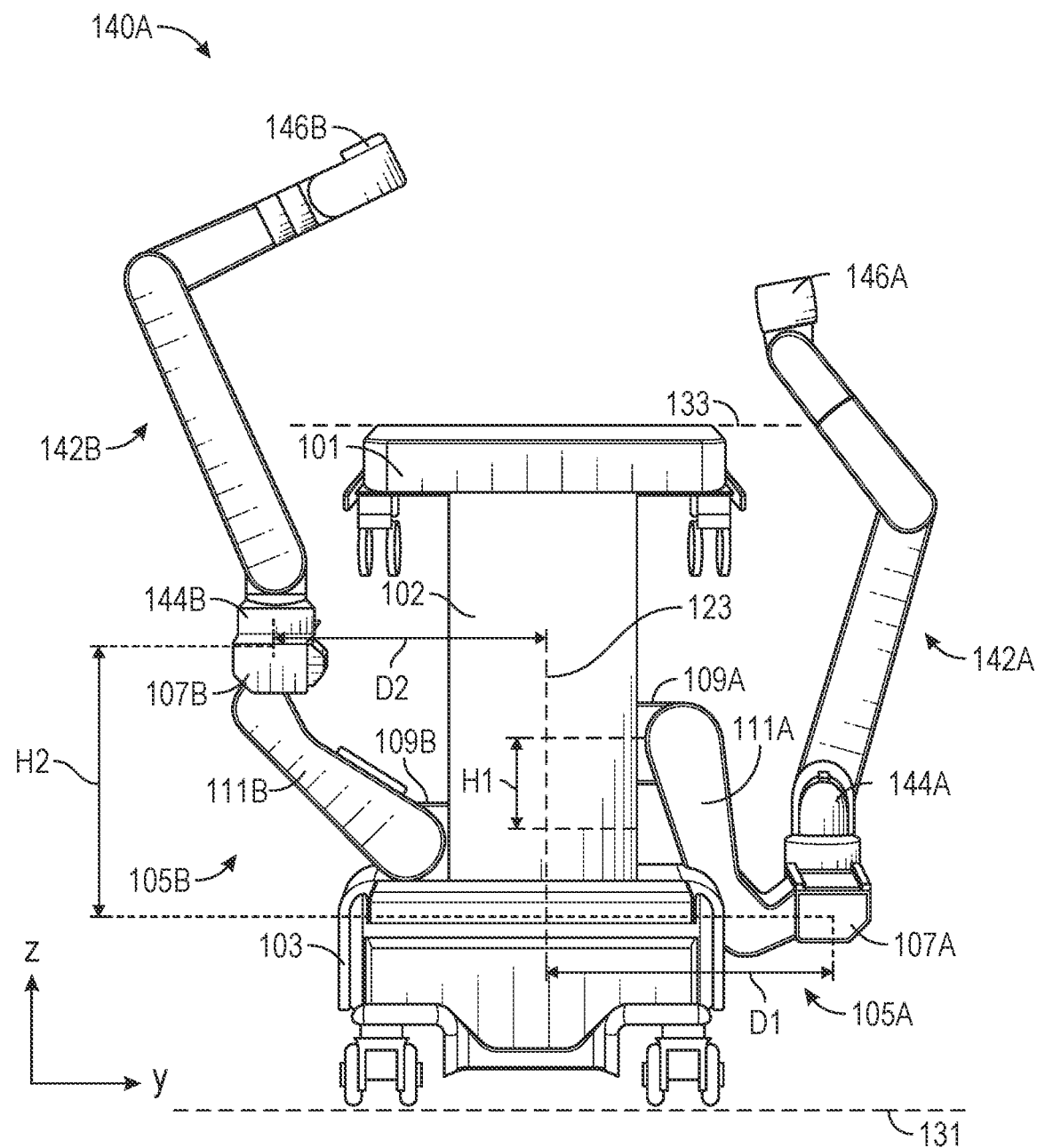
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
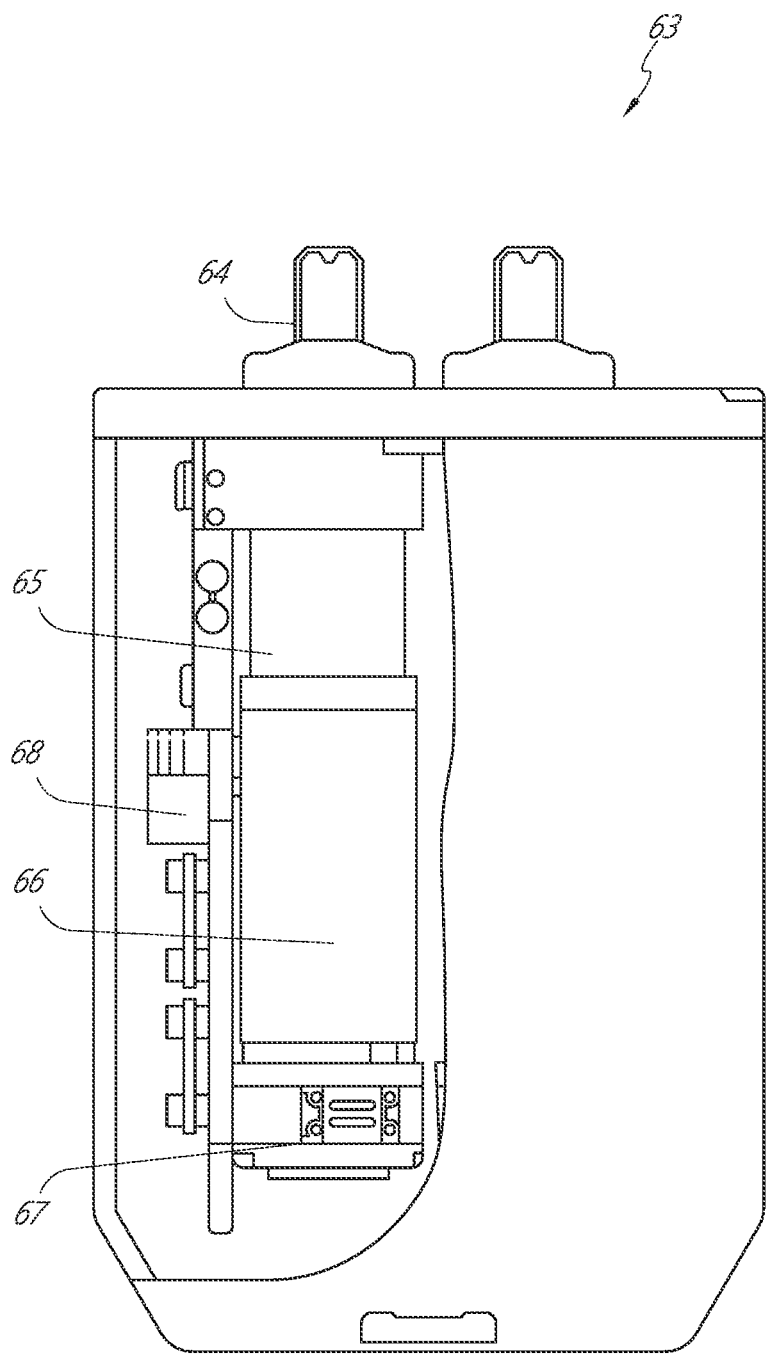
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
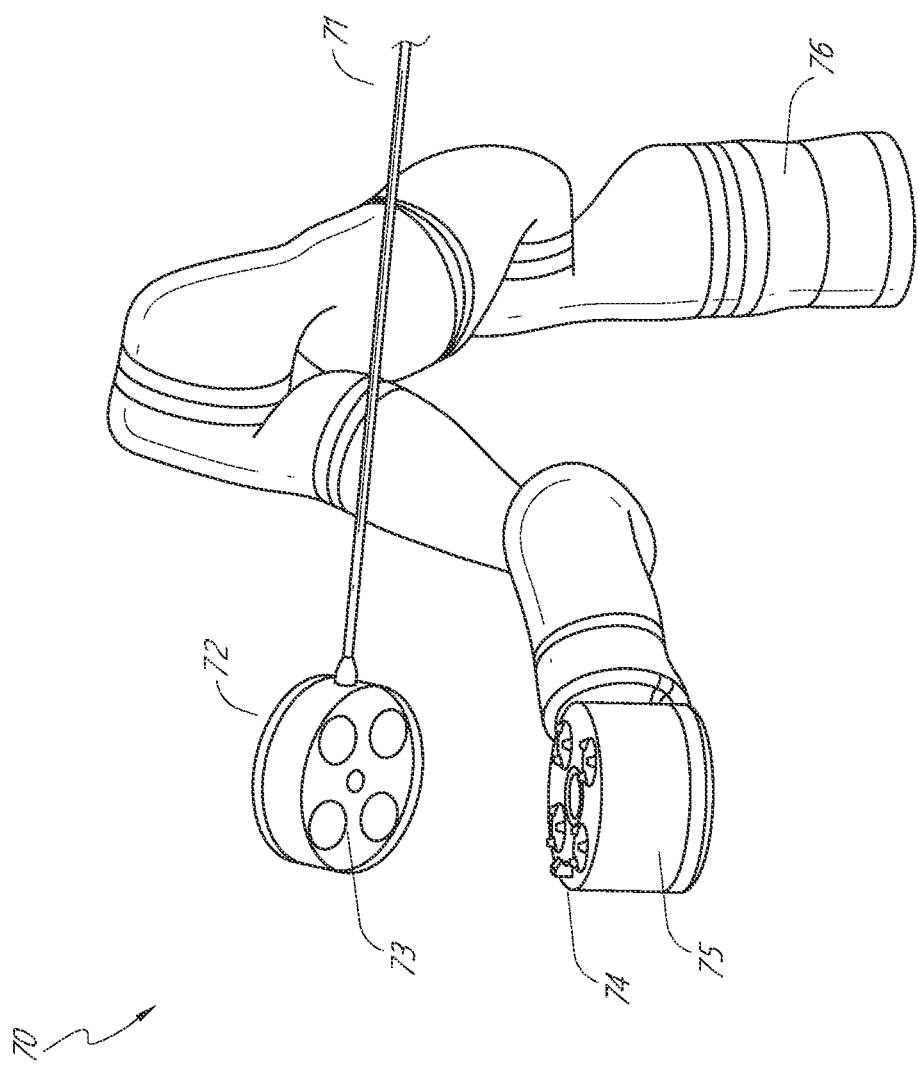
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
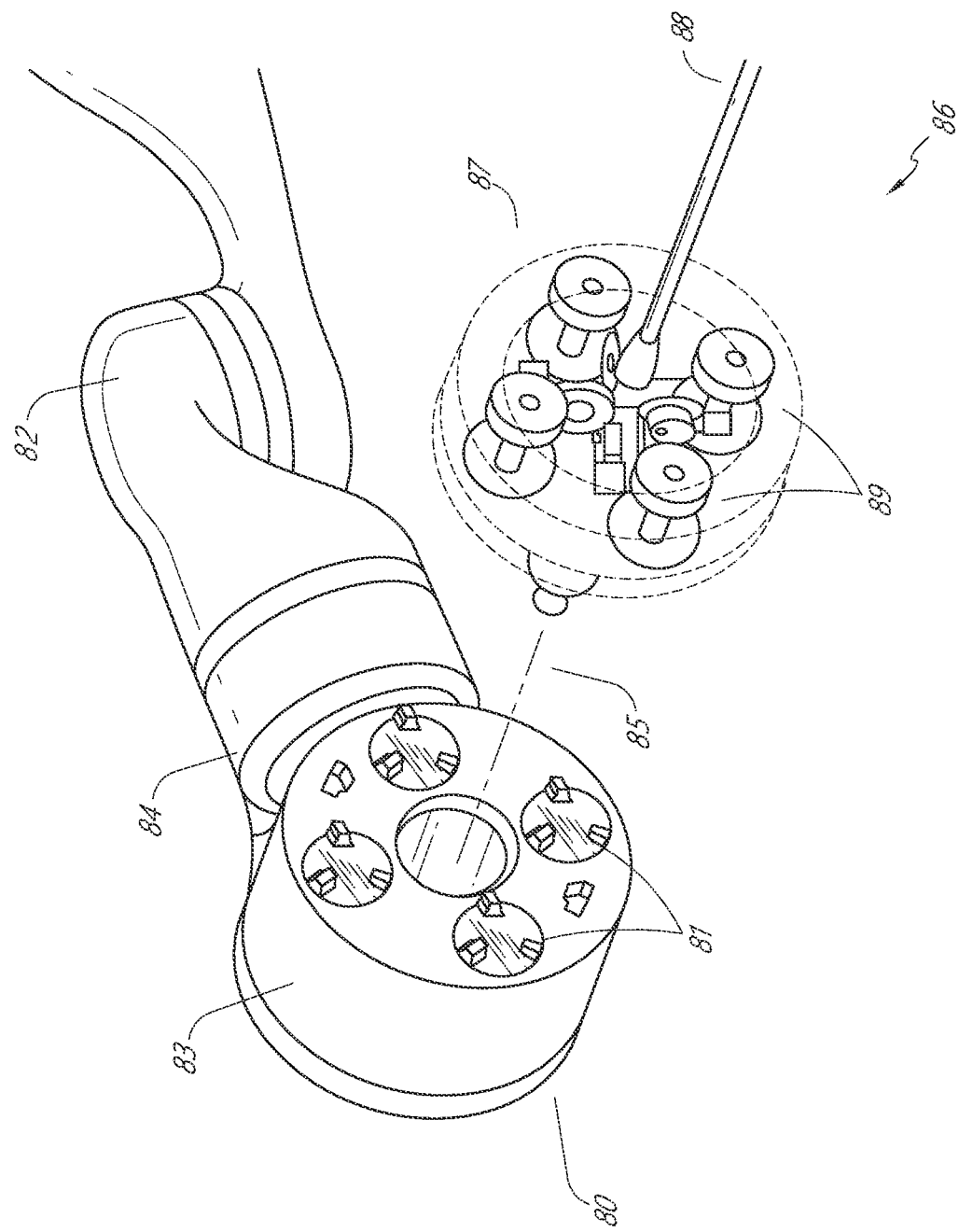
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
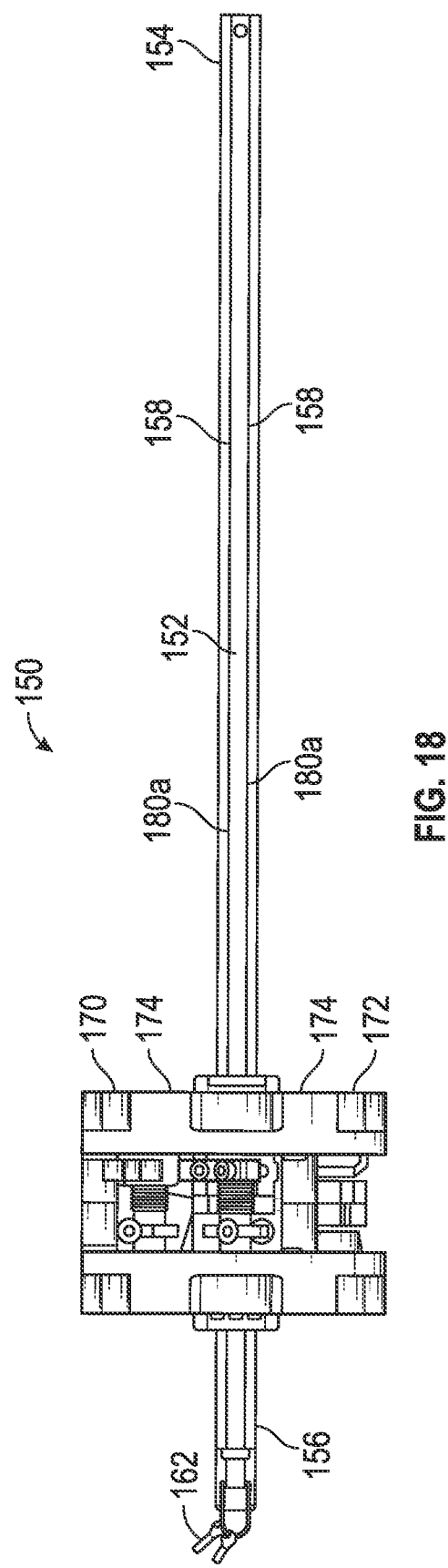
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
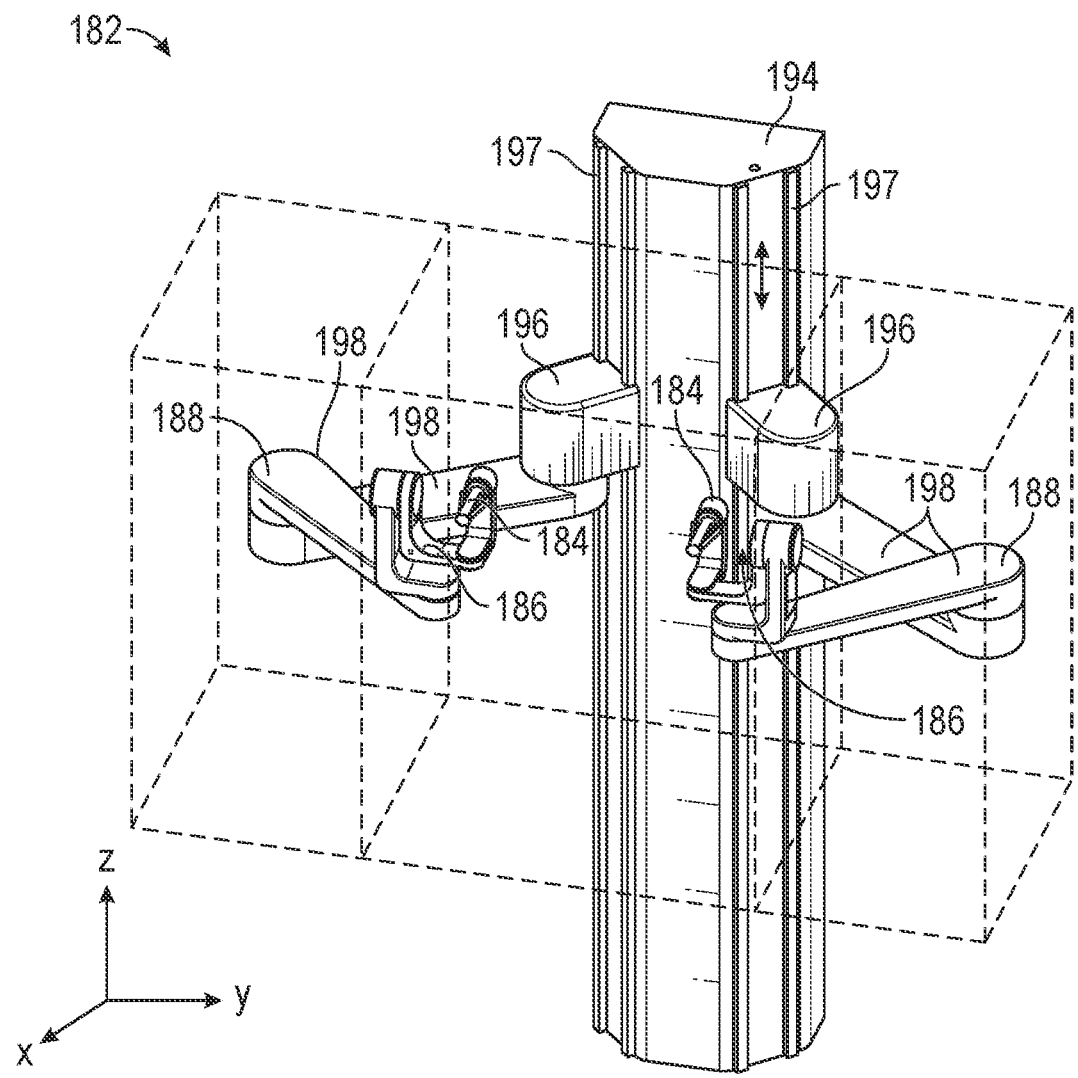
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
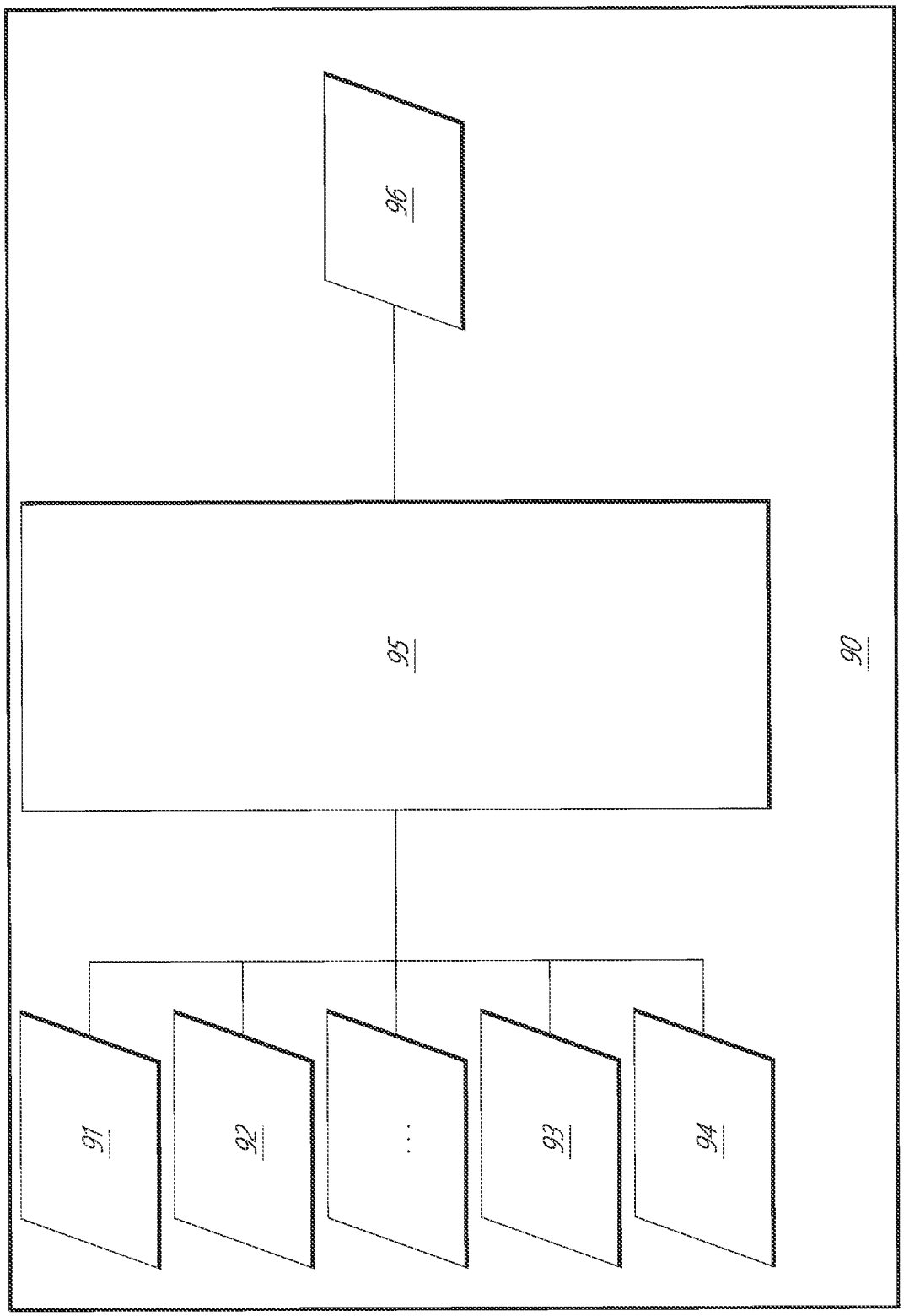
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Constrained Motion Control of Medical Instruments.

Embodiments of the disclosure relate to systems and techniques for constrained motion control of a medical instrument. As described herein, a robotic system (e.g., the system 10 of FIG. 1 or the system 140A of FIG. 14) can be used to control one or more medical instruments (e.g., steerable endoscope 13 of FIG. 1, medical instrument 34 of FIG. 4, or the instrument 150 of FIG. 18) using an input device (e.g., the controller 182 illustrated in FIG. 19) configured to receive user input for controlling movement of the instrument(s).

Different medical instruments may be capable of movement in different numbers of degrees-of-freedom (DOFs). When the number of DOFs in which a medical instrument is capable of movement differs from the number of DOFs in which the input device is capable of being manipulated by a user, there may be challenges in mapping the movement of the input device to commands for moving the medical instrument in the DOFs in which the medical device is capable of movement. For certain implementations, the medical instrument may be capable of movement in fewer DOFs than the input device. A medical instrument can be described as "under-actuated" when the medical instrument is constrained to move in fewer DOFs than may be beneficial for a particular task. For example, position and orientation can be viewed as a 6-DOF task (e.g., including the x, y, z, pitch, yaw, roll DOFs), certain medical instrument may be constrained to move in 5 or fewer DOFs, and thus, these medical instruments can be considered "under-actuated."

Figure 21:
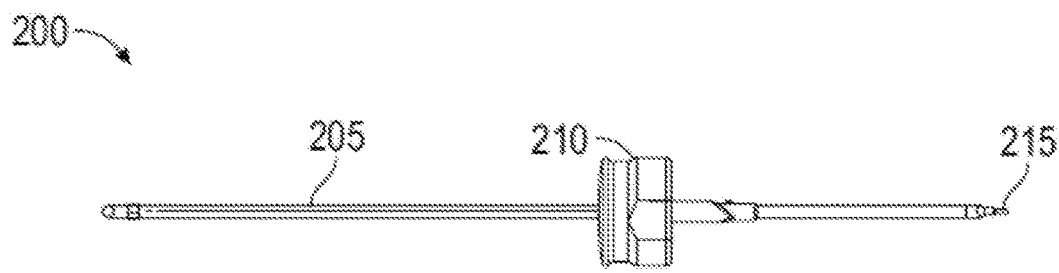
FIG. 21 illustrates an example of an under-actuated instrument that can be controlled by a robotic system in accordance with aspects of this disclosure.
Figure 22A:
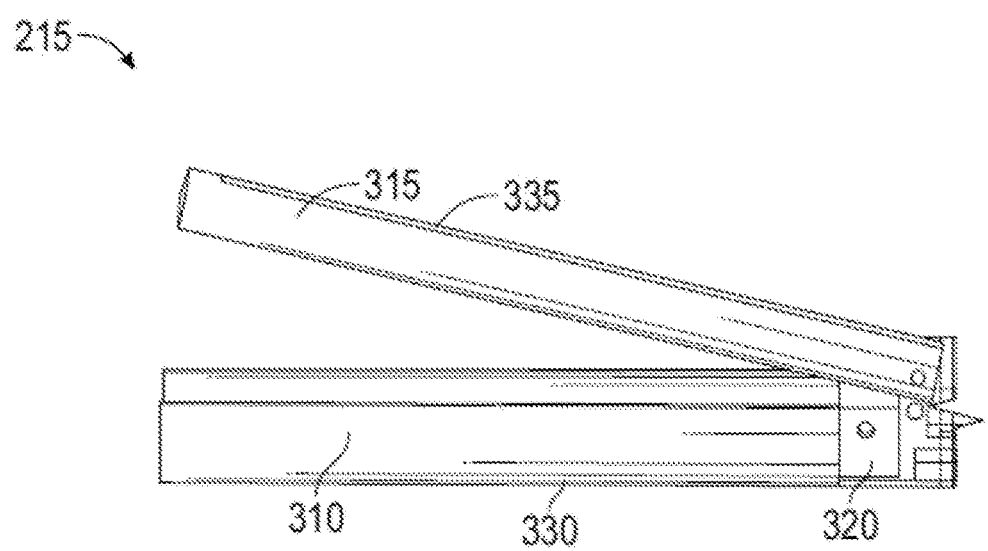
FIGS. 22A and 22B illustrate an end effector of the instrument of FIG. 21 in an open position and a closed position, respectively.
Figure 22B:
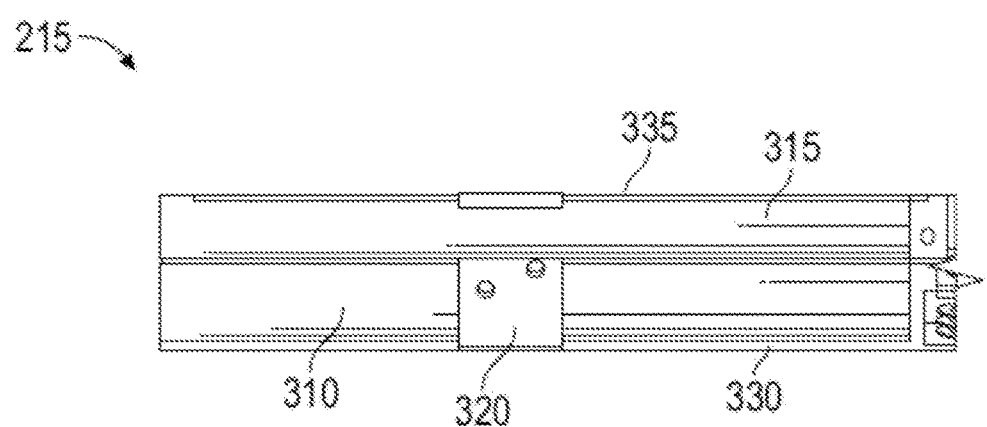

FIGS. 21-22B illustrate an example of an under-actuated instrument 200 that can be controlled by a robotic system in accordance with aspects of this disclosure. In particular, FIG. 21 provides an overall view of the instrument 200 while FIGS. 22A and 22B illustrate an end effector 215 of the instrument 200 in an open position and a closed position, respectively.

The instrument 200 can comprise a surgical stapler, which may benefit from being able to move in only 5-DOFs, rather than 6-DOFs. For example, a 5-DOF medical stapler may be capable of being designed with thicker and stiffer components than a corresponding 6-DOF stapler. Since surgical staplers may be used for clamping relatively thick materials, it can be beneficial for a surgical stapler to have thicker and stiffer components to handle the increased loads involved in clamping the relatively thick material. Another example of an under-actuated medical instrument is a suction irrigator, which may be constrained to move in 5-DOFs of movement, or even 4-DOFs of movement, depending on the implementation. In other implementations, the under-actuated medical instrument may be implemented as a straight harmonic tool or an articulating harmonic tool. The advantage of the present application extends to control of under-actuated instruments (including staplers and suction irrigators) beyond those contemplated here, including any others that may be available on the market, now and in the future.

In the implementation illustrated in FIG. 21, the medical instrument 200 includes a shaft 205, a handle 210, and an end effector 215. The instrument 200 can be coupled to any of the instrument drivers discussed above. One or more cables (not illustrated) can run along an outer surface of the shaft 205 and/or one or more cables can also run through the elongated shaft 205. Manipulation of the one or more cables (e.g., via an instrument driver) results in actuation of the end effector 215.

The handle 210, which may also be referred to as an instrument base, may generally comprise an attachment interface having one or more mechanical inputs, e.g., receptacles, pulleys or spools, that are designed to be reciprocally mated with one or more torque couplers on an attachment surface of an instrument driver.

Depending on the implementation of the particular instrument 200, the end effector 215 may be embodied to perform one or more different medical and/or surgical tasks, which can be effectuated via tensioning the one or more cables. In some embodiments, the instrument 200 comprises a series of pulleys to which the one or more cables can be operatively coupled that enable the shaft 205 to translate relative to the handle 210.

In some embodiments, the instrument 200 may include an end effector 215 adapted to transect and/or seal tissue. FIGS. 22A-22B illustrate an example embodiment wherein the end effector 215 is configured to function as a medical stapler in accordance with aspects of this disclosure. In particular, FIG. 22A illustrates the end effector 215 in an open position and FIG. 22B illustrates the end effector 215 in a closed position. As shown in FIGS. 22A and 22B, the end effector 215 in the illustrated embodiment includes a lower jaw 310, and upper jaw 315, and a firing mechanism 320. One or more grooves (not illustrated) may be formed in the upper jaw 315. Further, the lower jaw 310 (also referred to as a cartridge jaw) may include a lower jaw slot 330 and the upper jaw 315 may include an upper jaw slot 335. The firing mechanism 320 may include a tab and/or an I-beam in certain implementations. In certain embodiments, the firing mechanism 320 is configured to interact with a magazine (not illustrated) housing a plurality of staples (not illustrated) to drive the staples into tissue. In some embodiments, the firing mechanism can comprise a cantilevered member or push block.

As discussed above, the end effector 215 may be embodied as a medical stapler which can be used to seal and/or transect tissue. As shown in FIG. 22B, once the firing mechanism 320 has advanced transversely along the end effector 215 from the proximal end of the end effector 215, the end effector 215 will be clamped into the illustrated closed position. The medical instrument 300 can operate by clamping tissue between the two jaws (e.g., the lower jaw 310 and the upper jaw 315) of the medical instrument 300 and then pushing the firing mechanism 320 transversely along the lower jaw 310 and the upper jaw 315 to both form the staples and transect the tissue. Medical staplers such as the medical instrument 300 can be used, for example, in stomach stapling and/or roux-en-y gastric bypass procedures.

In some embodiments, the medical instrument may have a wrist configured to be articulated in 1 DOF. For certain medical procedures, for example, robotically controlled laparoscopic procedures, it is desirable to have a 2-DOF wrist. However, there may be design challenges associated with a 2-DOF wrist for a medical stapler which may not be present in a 1 DOF wrist. For example, it can be difficult to route the amount of force required to provide a sufficient clamping force to the jaws through the 2-DOF wrist. In addition, it can be difficult to provide control of the 2-DOF wrist (e.g., provide pitch and yaw DOF), while also independently controlling the stapler and firing mechanism separately from the 2-DOF movement of the wrist. Furthermore, staplers, whether manual or robotic, are often designed to be single-use (e.g., disposable), which can increase the costs associated with the staplers. Lastly, it can be difficult to design a medical stapler to have a low-profile, which can improve the maneuverability of the stapler in constricted spaces.

Figure 23:
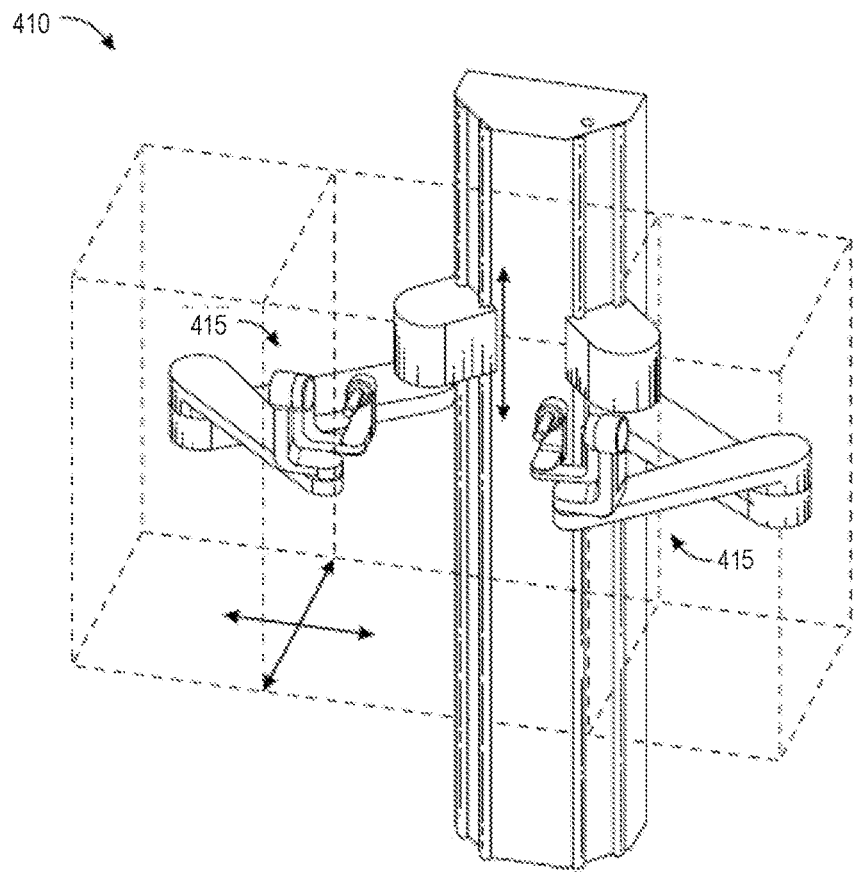
FIG. 23 illustrates an example input device which can be used to control movement of a medical instrument via one or more robotic arms in accordance with aspects of this disclosure.

When a medical instrument controlled by a robotic system has a reduced number of DOFs, the number of DOFs in which the medical instrument is capable of movement may not match the number of DOFs of an input device used by a user in controlling the medical instrument. FIG. 23 illustrates an example input device which can be used to control movement of a medical instrument via one or more robotic arms in accordance with aspects of this disclosure. The input device 410 of FIG. 23 may be similar to the controller 182 illustrated in FIG. 19. In particular, the input device 410 includes a pair of handles 415 which may be directly manipulated in space by a user's hands. In certain embodiments, each handle 415 may be capable of moving in 6 DOFs; however, in other implementations, the handle 415 may be capable of moving in a greater or fewer number of DOFs. For example, each of the handles 415 may be implemented as a gimbal. In some implementations, each of the gimbals may include or be operatively coupled to one or more motors configured to provide force feedback to the user. Such force feedback to the user may be used to reduce or limit the DOFs in which the gimbal may be moved by the user.

Figure 24:
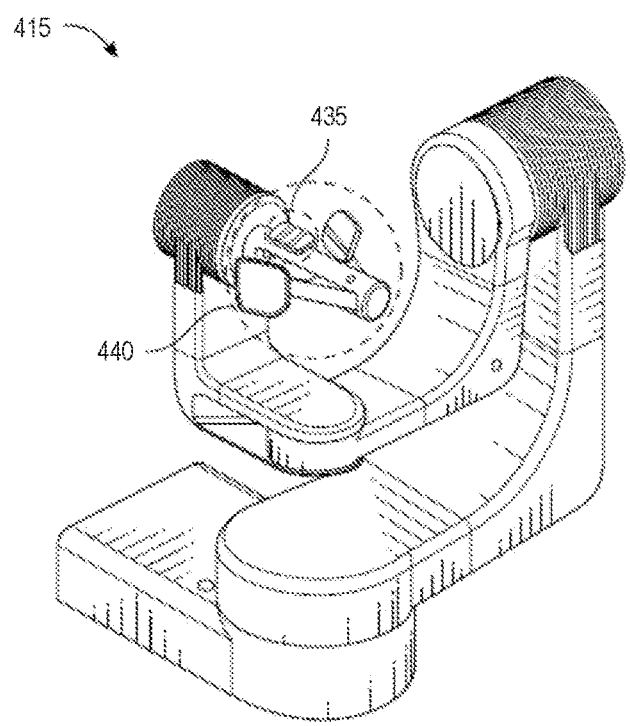
FIG. 24 illustrates a close-up view of one of the handles illustrated in FIG. 23 in accordance with aspects of this disclosure.

FIG. 24 illustrates a close-up view of one of the handles 415 illustrated in FIG. 23 in accordance with aspects of this disclosure. In some embodiments, the handle 415 includes a button 435 and finger-grips 440. The button 435 provides a user interface which allows the user to actuate an end effector of a corresponding medical instrument. The finger-grips 440 may provide an interface which allows the user to grab the handle 415 and manipulate the position of the handle 415 in three spatial DOFs. The handle 415 may also function as a gimbal allowing the user to manipulate the handle in the three orientation DOFs (e.g., pitch, yaw, and roll).

When a medical instrument is capable of moving in a different number of DOFs than an input device used to control movement of the medical instrument, there may be a challenge in mapping motions of the input device into motions that the medical instrument is capable of performing. In other words, it can be a challenge to control a medical instrument having different DOFs than the input device, whereby the kinematics of the input device do not match the kinematics (e.g., via 1:1 mapping) of the medical instrument. The challenge stems from the difficulty in accurately controlling a medical instrument that is unable to move as freely as the input device.

Aspects of this disclosure address at least two challenges in controlling medical devices using input devices capable of moving in a different number of DOFs. One challenge includes addressing so-called "undesired motion" (e.g., motion of the input device that the medical instrument is not capable of performing) which may occur using traditional kinematic chains between the master input device and the medical instrument. Another challenge involves providing feedback to a user regarding the motions of the input device which cannot be performed by the medical instrument.

2.1 Rejecting "Undesired Motion" Via a Modified Inverse Kinematics Algorithm

A robotic medical system generally receives a command to position an end effector of a medical instrument at a desired pose via an input device, such as one of the handles 415 of the input device 410 illustrated in FIGS. 23 and 24.

Figure 25:
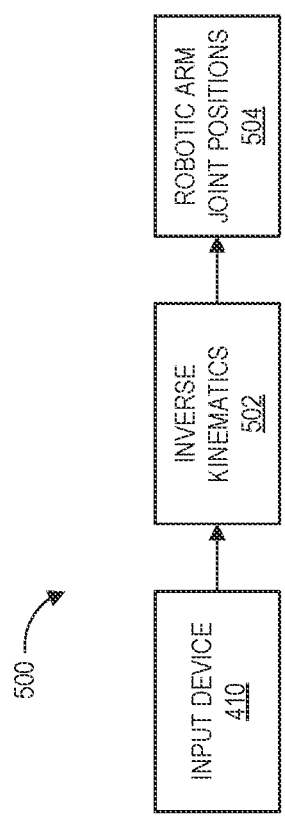
FIG. 25 illustrates an example block diagram illustrating how inverse kinematics can be used to determine the joint positions for a robotic arm in accordance with aspects of this disclosure.

The robotic system can use an inverse kinematics algorithm to generate the required positioning of each joint and/or actuator within one or more robotic arms to achieve the commanded end effector pose. FIG. 25 illustrates an example block diagram 500 illustrating how inverse kinematics 502 can be used to determine the joint positions for a robotic arm in accordance with aspects of this disclosure. In particular, the input device 410 can generate a commanded end effector pose based on the manipulation of the pose of the input device 410 by the user. The input device 410 provides the commanded end effector pose to the inverse kinematics 502, which determine a set of robotic arm joint positions 504 which can achieve the commanded end effector pose. The inverse kinematics 502 can be performed by a processor of the robotic system. These robotic arm joint positions 504 can be used to generate commands to position the robotic arm to achieve the desired end effector.

In executing the inverse kinematics 502 algorithms, the robotic system may use one or more Jacobians matrixes. A Jacobian matrix may define the dynamic relationship between two different representations of a system. The Jacobian matrix may be determined based on the time derivative of the kinematics questions that relate the joint positions of the robotic arm to the end effector pose. Thus, the Jacobian matrix can be used to relate the end effector velocities to the robotic arm joint angle velocities. An example of a Jacobian matrix is shown in equation (1) below:

$$\begin{bmatrix} v \\ \omega \end{bmatrix} = J\dot{q} \quad (1)$$

The vector on the left side of the equation is the twist of the end-effector and includes linear velocity v, and angular velocity $\omega$. $\dot{q}$ is the joint velocity vector or joint velocities of the robotic arm joints and J is the Jacobian matrix that relates the end effector twist to the joint velocities of the robotic manipulator. The Jacobian matrix may also be expressed as shown in equation (2) as follows:

$$J = \begin{bmatrix} J_v \\ J_\omega \end{bmatrix} \quad (2)$$

The Jacobian matrix represents a transformation that takes into consideration both linear velocity $J_v$ and angular velocity $J_\omega$. Since the medical procedure can be performed in a 3-D reference frame with x, y, z axes, the Jacobian matrix can ultimately be represented as follows, wherein $V_{x, y, z}$ represent linear velocities and $\omega_{x, y, z}$ represent angular velocities.

The transformation performed by the Jacobian matrix can apply for each DOF of an n-DOF system. For an end effector of a medical instrument, n may be the number DOFs in which the end effector is capable of movement, where each of the DOFs corresponds to the movement of a particular joint of the end effector system. For example, for an end effector of an instrument which is capable of movement in 5-DOF, (e.g., a surgical stapler), n will be equal 5. For the surgical stapler embodiment having 5-DOFs, the surgical stapler may be capable of movement in the roll, pitch, yaw, insertion, and instrument pitch DOFs, where the surgical stapler is not capable of movement in the instrument yaw DOF. Accordingly, for a 5-DOF instrument, to account for the transformation for each DOF n, the Jacobian matrix (shown in equation (3) below) will have five columns, wherein each column represents the transformation at a particular joint. In order, the columns correspond to roll, pitch, yaw, insertion, and instrument pitch.

$$J = \begin{bmatrix} J_{1,1} & \cdots & J_{1,m} \\ \vdots & \ddots & \vdots \\ J_{n,1} & \cdots & J_{n,m} \end{bmatrix} \quad (3)$$

The Jacobian illustrated above can be generic to medical instruments having different numbers of DoFs. For example, for a medical instrument capable of movement in 5 DoFs, n=5 and m=6. Thus, n may correspond to the number of DoFs in which the medical instrument is capable of movement while m may correspond to the number of DoFs in which the input device is capable of movement.

However, the use of the above Jacobian matrix along may not be sufficient to address undesired motion received from the input device. Accordingly, aspects of this disclosure relate to the use of a modified Jacobian matrix which can be used in an inverse kinematics algorithm to reject the undesirable motion included in a command received from the input device.

Figure 26:
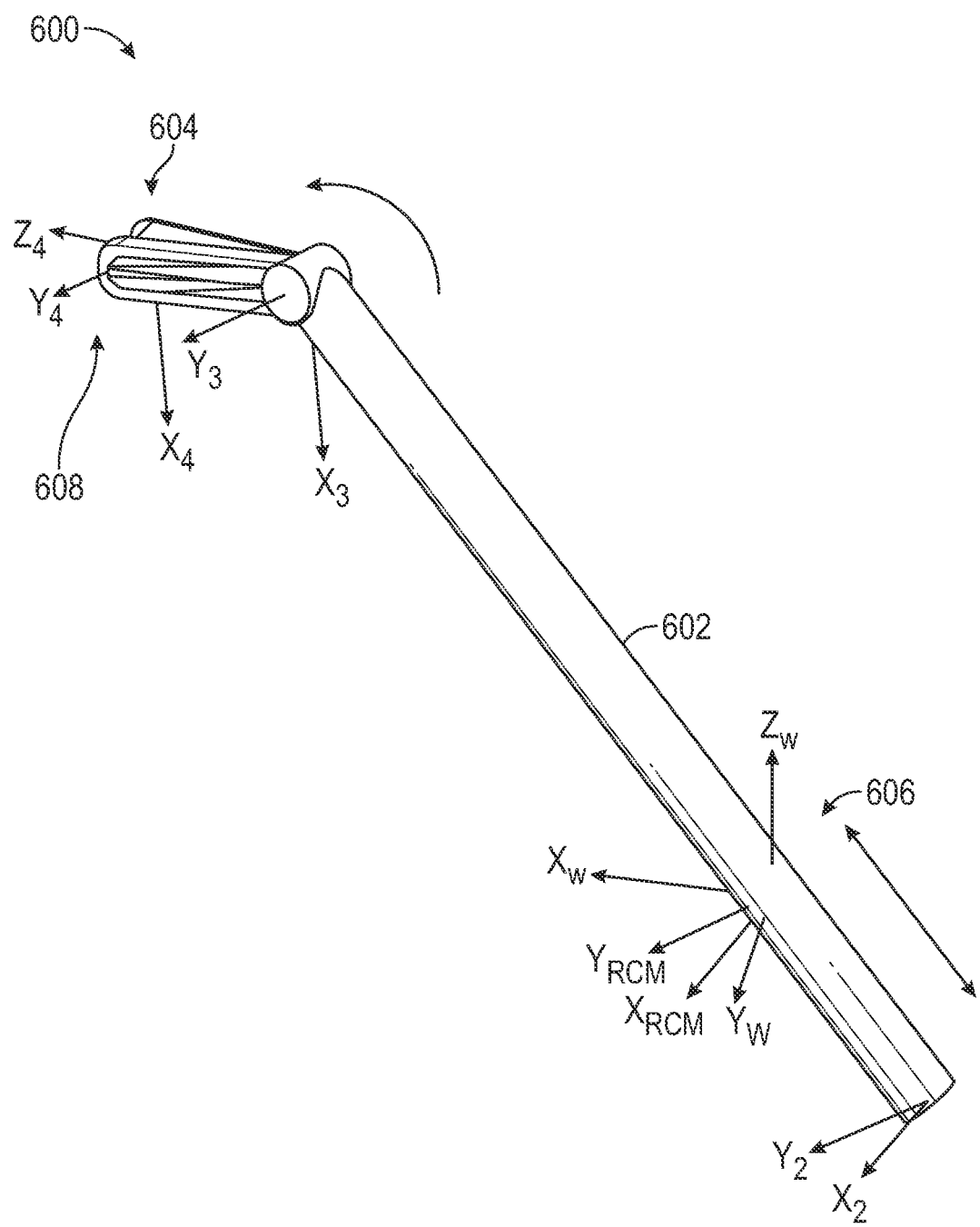
FIG. 26 illustrates the 5-DOF medical instrument with respect to different reference frames in accordance with aspects of this disclosure.

An example of an implementation of a modified inverse kinematics algorithm is provided in connection with a 5-DOF medical instrument below. FIG. 26 illustrates the 5-DOF medical instrument 600 with respect to different reference frames in accordance with aspects of this disclosure. In particular, the medical instrument 600 includes a shaft 602, which may be inserted through a cannula (not illustrated) to gain access to a patient's internal cavity, and an end effector 604. The direct kinematics for the 5-DOF medical instrument 600 for a representative pose of the medical instrument 600 can be defined as shown in equations (4)-(6) as follows:

$$q = \begin{bmatrix} \frac{\pi}{4} \\ \frac{\pi}{4} \\ \frac{\pi}{4} \\ -\frac{\pi}{4} \\ -50 \\ \frac{\pi}{4} \end{bmatrix} \quad (4)$$

$$R = Rot(q_1, x)Rot(q_2, Y)Rot(q_3, z)Rot(q_4, y) \quad (5)$$

$$p = Rot(q_1, x)Rot(q_2, Y)Rot(q_3, z)\begin{bmatrix} 0 \\ 0 \\ q_4 + l_1 \end{bmatrix} + R\begin{bmatrix} 0 \\ 0 \\ l_2 \end{bmatrix} \quad (6)$$

Where $q_i=1, \ldots 5$ are the components of vector q (e.g., the joint positions) and, without loss of generality, $l_1=200$ and $l_2=40$. The operator Rot(a,b) defines the 3×3 rotation matrix associated with angle "a" about axis "b". p is the position of the end-effector, e.g., the position of end-effector frame $(X_4, Y_4, Z_4)$ as shown in FIG. 26, $l_1$ is the fixed distance between frame $X_2, Y_2, Z_2$ and frame $X_3, Y_3, Z_3$ in FIG. 26, and $l_2$ is the fixed distance between $X_3, Y_3, Z_3$ and the end-effector frame $X_4, Y_4, Z_4$. These parameters are geometric parameters that define the tool dimensions. For example, $l_1$ defines the overall instrument shaft length, and $l_2$ defines, for example, the length of the jaw of the end effector. By varying these parameters different tools can be designed and built for different applications. The system may define two Jacobian matrixes used in the modified inverse kinematics algorithms for rejecting unwanted motion. A first Jacobian matrix 606 may be defined in the world frame while a second Jacobian matrix 608 may be defined in the end effector frame.

The first Jacobian matrix 606 describes the coupling between the Cartesian speeds in the world frame and the joint speeds for all of the joints in the kinematic chain that defines the position of the end effector. The kinematic chain may include the joints of the robotic arm controlling the medical instrument and the joints of the medical instrument. The second Jacobian matrix 608 describes the coupling between the end effector Cartesian speeds and the joint speeds. In the end effector frame, the end effector 604 Cartesian speeds may be directly mapped to the motion of the input device due to manipulation of the input device by the user, for example, by relating the frame of reference of the end effector to the world frame of reference of the robotic system. Thus, the movement of the input device may ideally be mapped one-to-one with the Cartesian directions of the end effector 604. The first Jacobian matrix 606 may define a remote center of motion (RCM) where movement of the cannula is constrained, for example, to prevent the cannula from exerting excessive force onto the patient's body wall. Accordingly, each of the first and second Jacobian matrixes 606 and 608 may constrain the motion of the medical instrument 600, the first Jacobian matrix 606 constraining motion of the medical instrument 600 to maintain the RCM and the second Jacobian matrix 608 constraining motion of the end effector to follow the motion of the input device.

Below are examples of the first Jacobian matrix 606 and the second Jacobian matrix 608 for a given pose of the medical instrument 600. When the medical instrument 600 has a different pose, the specific value of the first and second Jacobian matrixes 606 and 608 will be different. The first Jacobian matrix 606 is shown in equation (7) below:

$$J = \begin{bmatrix} 0 & 111.9239 & 14.1421 & 0.7071 & -5.8579 \\ -65.0000 & 99.1421 & 24.1421 & -0.5000 & 10.0000 \\ -93.2843 & -99.1421 & 4.1421 & 0.5000 & -38.2843 \\ 1.0000 & 0 & 0.7071 & 0 & 0.5000 \\ 0 & 0.7071 & -0.5000 & 0 & 0.8536 \\ 0 & 0.7071 & 0.5000 & 0 & 0.1464 \end{bmatrix} \quad (7)$$

The second Jacobian matrix 608 is shown in equation (8):

$$J\_ee = \begin{bmatrix} 73.0330 & 103.2843 & 0.0000 & -0.7071 & 40.0000 \\ -69.1421 & 126.0660 & 28.2843 & 0.0000 & -0.0000 \\ 53.0330 & 75.0000 & 0.0000 & 0.7071 & -0.0000 \\ -0.1464 & -0.5000 & -0.7071 & 0 & -0.0000 \\ 0.5000 & 0.7071 & 0.0000 & 0 & 1.0000 \\ 0.8536 & -0.5000 & 0.7071 & 0 & -0.0000 \end{bmatrix} \quad (8)$$

The values in the second Jacobian matrix 608 may relate to the ability of the end effector 604 to move from the medical instrument's 600 current pose. For example, for the 5-DOF medical instrument 600, the medical instrument 600 may not have the ability to move in the yaw DOF. Since the medical instrument 600 is capable of movement in the pitch DOF, the values in the fifth row of the second Jacobian matrix 608 reflect the ability of the medical instrument to pitch. Likewise, because the medical instrument 600 is incapable of movement in the yaw DOF, the values in the fourth row of the second Jacobian matrix 608 reflect the inability of the medical instrument to yaw (e.g., the zeros in the fourth and fifth columns in the fourth row).

In certain implementations, the robotic system can reject unwanted motion in the inverse kinematics by modifying an input command received from the input device via discarding a portion of the input command corresponding to a movement of the end effector that is not achievable. For example, the robotic system can remove the row(s) of the second Jacobian matrix 608 that will not produce any motion at the end effector. Thus, after defining the first and second Jacobian matrixes 606 and 608 for the current pose of the medical instrument 600, the system can modify the second Jacobian matrix 608 by discarding the row(s) of the second Jacobian matrix 608 that describes the inability of the medical instrument 600 to perform the unwanted motion. When the input device has n more DOFs than that of the medical instrument, the system can discard n rows of the second Jacobian matrix 608 corresponding to the n DOFs in which the medical instrument is incapable of movement. For example, the discarded rows of the second Jacobian matrix 608 may correspond to one or more types of movement of which the instrument is incapable.

In the example of the second Jacobian matrix 608 provided above for the 5-DOF medical instrument that does not have the ability to yaw, the fourth row can be discarded since the end effector 604 cannot move in the yaw DOF. An example of the above second Jacobian matrix 608 in which the fourth row is identified as including unwanted motion is shown in equation (9):

$$J\_ee = \begin{bmatrix} 73.0330 & 103.2843 & 0.0000 & -0.7071 & 40.0000 \\ -69.1421 & 126.0660 & 28.2843 & 0.0000 & -0.0000 \\ 53.0330 & 75.0000 & 0.0000 & 0.7071 & -0.0000 \\ -0.1464 & -0.5000 & -0.7071 & 0 & -0.0000 \\ 0.5000 & 0.7071 & 0.0000 & 0 & 1.0000 \\ 0.8536 & -0.5000 & 0.7071 & 0 & -0.0000 \end{bmatrix} \quad (9)$$

An example of the above second Jacobian matrix 608 modified by discarding the fourth row is shown in the following equation (10):

$$J\_ee\_5by\_5 = \begin{bmatrix} 73.0330 & 103.2843 & 0.0000 & -0.7071 & 40.0000 \\ -69.1421 & 126.0660 & 28.2843 & 0.0000 & -0.0000 \\ 53.0330 & 75.0000 & 0.0000 & 0.7071 & -0.0000 \\ 0.5000 & 0.7071 & 0.0000 & 0 & 1.0000 \\ 0.8536 & -0.5000 & 0.7071 & 0 & -0.0000 \end{bmatrix} \quad (10)$$

In some implementations, it is not necessary to modify the first Jacobian matrix 606 because the medical instrument 600 may always be able to at least partially perform a portion of the commanded end effector motion in the word frame defined by the first Jacobian matrix 606.

Figure 27:
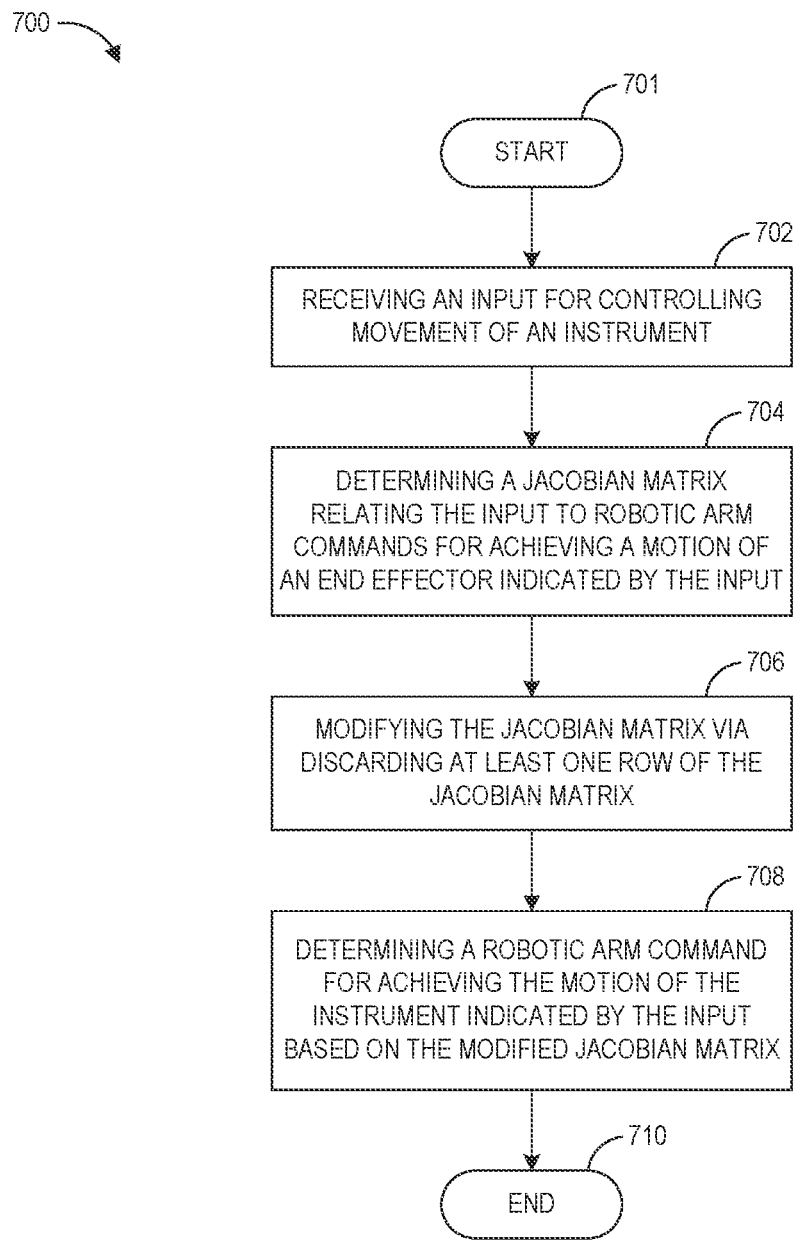
FIG. 27 is a flowchart illustrating an example method operable by a robotic system, or component(s) thereof, for performing constrained motion control of medical instruments in accordance with aspects of this disclosure.

FIG. 27 is a flowchart illustrating an example method operable by a robotic system, or component(s) thereof, for performing constrained motion control of medical instruments in accordance with aspects of this disclosure. For example, the steps of method 700 illustrated in FIG. 27 may be performed by processor(s) and/or other component(s) of a medical robotic system (e.g., robotically-enabled system 10, or one of the robotic medical systems 200, 300, or 400 discussed above) or associated system(s). For convenience, the method 700 is described as performed by the "system" in connection with the description of the method 700.

The method 700 begins at block 701. At block 702, the system receives, via an input device, an input for controlling movement of a medical instrument. The instrument has a different number of DOFs than the input device. For example, in some implementations the instrument is capable of movement in a fewer number of DOFs that the input device, however, in other implementations, the instrument may be capable of movement in a greater number of DOFs that the input device. In certain implementations, the system can also transform the input received from the input device into an end effector coordinate frame.

At block 704, the system determines a Jacobian matrix relating the input to the input device to robotic arm commands for achieving a motion of the end effector indicated by the input. For example, the Jacobian matrix may define the dynamic relationship between the end effector Cartesian speeds and the joint speeds for all of the joints in the kinematic chain that defines the position of the end effector.

At block 706, the system modifies the Jacobian matrix via discarding at least one row of the Jacobian matrix. For example, the system may discard one or more rows of the Jacobian matrix corresponding to types of movement of which the instrument is incapable of performing. In some implementations, the number of rows discarded from the Jacobian may correspond to the difference between the number of DOFs of the input device and the number of DOFs of the medical instrument. In one example, the end effector may be incapable of movement in a yaw degree-of-freedom and the system may modify the Jacobian matrix by discarding a row of the Jacobian matrix corresponding to the yaw movement.

At block 708, the system determines a robotic arm command for achieving the motion of the instrument indicated by the input based on the modified Jacobian matrix. For example, the system can determine the robotic arm command including commanded joint positions for the robotic arm using inverse kinematics to determine the robotic arm command. The inverse kinematics may use the modified Jacobian matrix as a part of the inverse kinematics algorithm. For example, the inverse kinematics algorithm may include inverting the modified Jacobian matrix, determining the joint speeds for all of the joints in the kinematic chain using the inverted modified Jacobian matrix (e.g., using equation (1) above), and generating the robotic arm command using the determined joint speeds. In another example, the inverse kinematics algorithm may include inverting the end effector Jacobian matrix, modify the inverted end effector Jacobian matrix by removing a component of an angular velocity from the inverted end effector Jacobian matrix, and determining joint velocities for joints of the robotic arm based on the modified inverted end effector Jacobian matrix. The method 700 ends at block 710.

Aspects of this disclosure in which the system is configured to reject unwanted motion may accomplish two fundamental tasks. First, the system may only reject motions that the medical instrument is unable to accomplish for any given pose. Second, the system may project the user motions onto a subset of motions that the instrument is able to accomplish. That is, even though portions of the user's manipulation of the input device may correspond to movements that the medical instrument in incapable of performing, the system is able to map the instructed movements at the input device onto the set of movements that the medical instrument is capable of performing. Thus, the system is able to follow the commanded movements to the extent that the medical instrument is capable.

The methods and algorithms described herein can be generalized for any medical instrument with any number of degrees of freedom less than the traditional 6-DOFs. Depending on limitations of the specific medical instrument, the correct row(s) of the Jacobian matrix will be discarded from the end effector Jacobian matrix. For example, for an instrument that can yaw but not pitch, the system will discard the fifth row of the end effector Jacobian matrix.

2.2. Alignment of the Input Device and the End Effector

As discussed herein, certain medical instruments may be capable of movement in a fewer number of DOFs that an input device used to control the medical instrument. Because of this difference, it may be possible for a user to manipulate the input device into a pose for which the end effector of the medical instrument is unable to duplicate. In order to provide an intuitive interface for the user, the pose of the input device should match the pose of the medical instrument as closely as possible. However, since the input device may not be restricted to the same movements as the medical instrument, if the user poses the input device in a manner that the medical instrument cannot follow, the user may be disoriented and/or have difficulty conceptualizing the mismatch between the input device pose and the medical instrument end effector pose.

In order to address the above-indicated challenge, aspects of this disclosure relate to systems and methods for aligning the pose of the input device to the pose of the end effector. For example, the robotic system can be configured to ensure that the surgeon's hand is always aligned with the end effector of the medical instrument by constraining motion of the input device. For example, the robotic system may identify whether a commanded motion of the end effector cannot be accomplished and constrain the movement of the input device.

Figure 28:
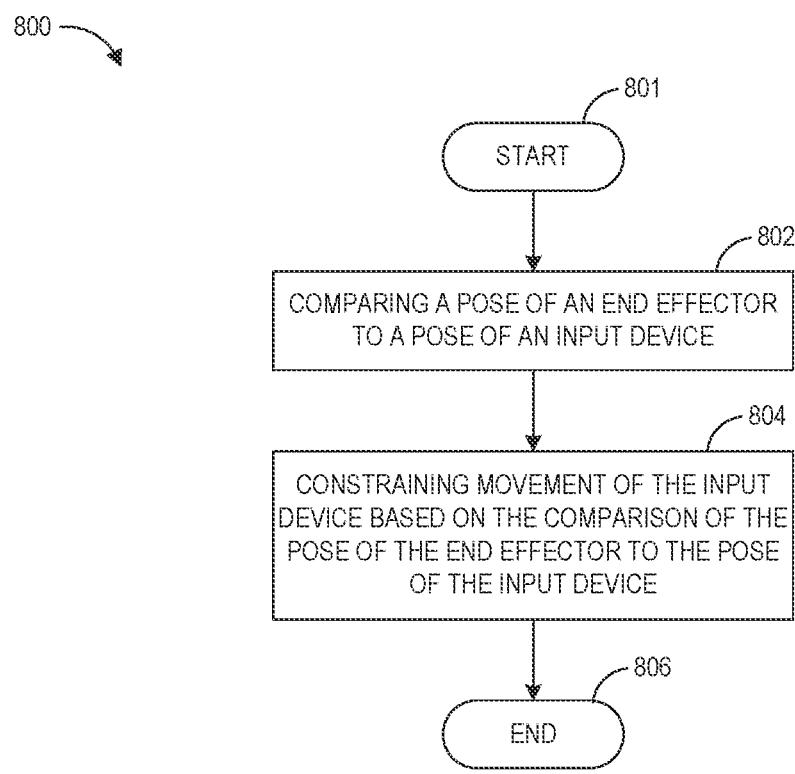
FIG. 28 is a flowchart illustrating an example method operable by a robotic system, or component(s) thereof, for aligning an input device and an end effector of a medical instrument in accordance with aspects of this disclosure.

FIG. 28 is a flowchart illustrating an example method operable by a robotic system, or component(s) thereof, for aligning an input device and an end effector of a medical instrument in accordance with aspects of this disclosure. For example, the steps of method 800 illustrated in FIG. 28 may be performed by processor(s) and/or other component(s) of a medical robotic system (e.g., robotically-enabled system 10, or one of the robotic medical systems 200, 300, or 400 discussed above) or associated system(s). For convenience, the method 800 is described as performed by the "system" in connection with the description of the method 800.

The method 800 begins at block 801. At block 802, the system compares a pose of the end effector to a pose of the input device. For example, the system may determine whether there is any difference between the pose of the end effector and the pose of the input device. If the poses of the end effector and the input device are the same, the system may not need to constrain movement of the input device.

At block 804, the system constrains movement of the input device based on the comparison of the pose of the end effector to the pose of the input device. For example, if the pose of the input device is not the same as the pose of the end effector, the system may constrain further movement of the input device away from the pose of the end effector. In some implementations, the input device may provide "force feedback" via one or more actuators included in the input device. The force feedback may be configured to move the input device toward the pose of the end effector. In some implementations, the force feedback may provide a force that the user can feel through manipulation of the input device. In other implementations, the force feedback may prevent the user from moving the input device in a direction away from the pose of the end effector. Thus, the force feedback can be configured to constrain a clinician's hand to move the input device in a constrained motion. The motion of the input device can be constrained in the same DOF in which motion of the end effector is constrained.

In certain implementations, the system can constrain movement of the input device by transforming the DOF in which the end effector movement is constrained from the end effector coordinate frame into a coordinate frame of the input device. For example, the system can receive the pose of the end effector and determine the Jacobian matrix in the end effector frame. Within the end effector frame, the system can identify the axis about which the end effector cannot rotate. Due to the physical construction of the input device, the axis in which the end effector cannot rotate may not align with any of the physical joints of the input device. Thus, in certain configuration, it may not be sufficient to simply prevent rotation about one motor of the input device since that may impede motions that are achievable by the end effector.

In order to constrain motion of the input device corresponding to the motions that the end effector is incapable of, the system can transform the DOF in which the end effector is constrained into the frame of the input device and freeze motion in the transformed DOF. The system can also apply force feedback to all other DOFs in the input device frame to ensure that the input device and the end effector are always aligned. The projection into the input device frame improves performance and user's experience by preventing the user from moving the input device to far out of alignment with the end effector pose before the force feedback brings the input device back into alignment with the end effector pose. Without such alignment using force feedback, the user may constantly be pulled back to a certain pose instead of being prevented from moving in a certain direction and guided along acceptable motion trajectories.

3. Implementing Systems and Terminology.

Implementations disclosed herein provide systems, methods and apparatus for constrained motion control of medical instruments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for constraining the motion of medical instruments described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system, comprising:
   an instrument having an end effector;
   a robotic arm configured to control movement of the instrument and the end effector;
   an input device configured to receive an input for controlling movement of the instrument and the end effector, wherein the instrument is capable of moving in a fewer number of degrees-of-freedom (DOFs) than the input device, wherein the input device comprises a gimbal configured to receive force feedback that constrains a clinician's hand to move the gimbal in a constrained motion that is constrained to the fewer number of DOFs;
   at least one processor; and
   at least one computer-readable memory in communication with the at least one processor and having stored thereon computer-executable instructions to cause the at least one processor to:
   determine a Jacobian matrix relating the input to robotic arm commands for achieving a motion of the end effector indicated by the input,
   modify the Jacobian matrix by discarding at least one row of the Jacobian matrix corresponding to a DOF in which the instrument is incapable of movement, and
   determine a robotic arm command for achieving the motion of the end effector indicated by the input based on the modified Jacobian matrix.

2. The robotic system of claim 1, wherein the input device has 6 DOFs and the instrument has 5 DOFs.

3. The robotic system of claim 1, wherein:
the input device has n more DOFs than the instrument; and
the modifying of the Jacobian matrix comprises discarding n rows of the Jacobian matrix corresponding to one or more types of movement of which the instrument is incapable of moving.

4. The robotic system of claim 1, wherein the instrument is a surgical stapler, suction irrigator, straight harmonic tool, or articulating harmonic tool.

5. The robotic system of claim 1, wherein the instrument comprises a surgical stapler having 5 DOFs.

6. The robotic system of claim 1, wherein the instrument comprises a suction irrigator having at least 4 DOFs.

7. The robotic system of claim 1, wherein:
the DOF in which the instrument is incapable of movement is a yaw DOF of the end effector, and
the modifying of the Jacobian matrix comprises discarding a row of the Jacobian matrix corresponding to yaw movement.

8. The robotic system of claim 1, wherein the input device is capable of movement in the DOF in which the instrument is incapable of movement, and wherein the constrained motion of the gimbal restricts motion of the gimbal in the DOF in which the instrument is incapable of movement.

9. The robotic system of claim 1, wherein:
the instrument is constrained in movement at a remote center of motion (RCM);
the Jacobian matrix comprises an end effector Jacobian matrix that relates the input to the input device to the robotic arm commands for achieving the motion of the end effector indicated by the input; and
the computer-executable instructions further cause the at least one processor to:
modify the end effector Jacobian matrix based on discarding the at least one row from the end effector Jacobian matrix;
determine an RCM Jacobian matrix relating the input to the input device to the robotic arm commands for maintaining the RCM; and
determine the robotic arm command based on the modified end effector Jacobian matrix and the RCM Jacobian matrix.

10. The robotic system of claim 1, wherein the Jacobian matrix relates a frame of reference of the end effector to a world frame of reference of the robotic system.

11. A method for controlling movement of an end effector of a medical instrument, the method comprising:
receiving, via an input device, an input for controlling movement of the instrument, wherein the instrument has a fewer number of degrees-of-freedom (DOFs) than the input device, wherein the input device comprises a gimbal configured to receive force feedback;
determining a Jacobian matrix relating the input received via the input device to robotic arm commands for achieving a motion of the end effector indicated by the input;
modifying the Jacobian matrix by discarding at least one row of the Jacobian matrix, wherein the row corresponds to a DOF in which the instrument is incapable of movement;
determining a robotic arm command for achieving the motion of the end effector indicated by the input based on the modified Jacobian matrix; and
providing force feedback to the gimbal that constrains a motion of the gimbal to the fewer number of degrees of freedom.

12. The method of claim 11, wherein the input device has 6 DOFs and the end effector has 5 DOFs.

13. The method of claim 11, wherein:
the input device has n more DOFs than the instrument; and
the modifying of the Jacobian matrix comprises discarding n rows of the Jacobian matrix corresponding to types of movement of which the instrument is incapable of moving.

14. The method of claim 11, wherein:
the DOF in which the instrument is incapable of movement is a yaw DOF of the end effector, and
the modifying of the Jacobian matrix comprises discarding a row of the Jacobian matrix corresponding to the yaw DOF.

15. The method of claim 11, wherein the input device is capable of movement in the DOF in which the instrument is incapable of movement, and wherein the constrained motion of the gimbal restricts motion of the gimbal in the DOF in which the instrument is incapable of movement.

16. A robotic system, comprising:
an instrument having an end effector;
a robotic arm configured to control movement of the end effector;
a gimbal configured to receive an input for controlling movement of the end effector, wherein the end effector has fewer degrees-of-freedom (DOFs) than the gimbal;
at least one processor; and
at least one computer-readable memory in communication with the at least one processor and having stored thereon computer-executable instructions to cause the at least one processor to:
determine a Jacobian matrix relating the input to robotic arm commands for achieving a motion of the end effector indicated by the input,
discard at least one row of the Jacobian matrix based on a DOF in which the gimbal is capable of movement and the end effector is incapable of movement,
determine a robotic arm command for achieving the motion of the instrument indicated by the input based on the Jacobian matrix after the at least one row is discarded, and
provide force feedback to the gimbal that constrains motion of the gimbal to the fewer DOFs of the end effector.

17. The robotic system of claim 16, wherein the gimbal is capable of movement in the DOF in which the end effector is incapable of movement, and wherein the force feedback restricts motion of the gimbal in the DOF in which the instrument is incapable of movement.

18. The robotic system of claim 16, wherein the end effector is incapable of yaw movement, and the force feedback restricts yaw movement of the gimbal.

* * * * *